US012661079B2

(12) United States Patent
Menon et al.

(10) Patent No.: US 12,661,079 B2
(45) Date of Patent: Jun. 23, 2026

(54) SYSTEM AND METHODS OF PREDICTION OF ISCHEMIC BRAIN TISSUE FATE FROM MULTI-PHASE CT-ANGIOGRAPHY IN PATIENTS WITH ACUTE ISCHEMIC STROKE USING MACHINE LEARNING

(71) Applicant: Circle Cardiovascular Imaging Inc., Calgary (CA)

(72) Inventors: Bijoy K. Menon, Calgary (CA); Wu Qiu, Calgary (CA); Mayank Goyal, Calgary (CA); Michael Hill, Calgary (CA); Andrew Demchuk, Calgary (CA); Alireza Sojoudi, Calgary (CA)

(73) Assignee: Circle Cardiovascular Imaging Inc., Calgary (CA)

( * ) Notice: Subject to any disclaimer, the term of this patent is extended or adjusted under 35 U.S.C. 154(b) by 484 days.

(21) Appl. No.: 18/303,241

(22) Filed: Apr. 19, 2023

(65) Prior Publication Data

US 2023/0329659 A1 Oct. 19, 2023

Related U.S. Application Data

(63) Continuation of application No. 17/906,169, filed as application No. PCT/CA2021/050320 on Mar. 10, 2021, now Pat. No. 12,465,313.

(Continued)

(51) Int. Cl.
*A61B 6/00* (2024.01)
*A61B 6/50* (2024.01)
(Continued)

(52) U.S. Cl.
CPC ............ *A61B 6/5217* (2013.01); *A61B 6/501* (2013.01); *A61B 6/5235* (2013.01);
(Continued)

(58) Field of Classification Search
None
See application file for complete search history.

(56) References Cited

U.S. PATENT DOCUMENTS

| | | | |
|---|---|---|---|
| 2013/0243291 A1 | 9/2013 | Varsha et al. | |
| 2016/0157800 A1 | 6/2016 | Goyal et al. | |

(Continued)

FOREIGN PATENT DOCUMENTS

| | | | | |
|---|---|---|---|---|
| CN | 107613915 A | 1/2018 | | |
| WO | WO-2006002312 A2 * | 1/2006 | ............. | A61B 6/481 |

(Continued)

OTHER PUBLICATIONS

USPTO, Office Action for corresponding U.S. Appl. No. 17/906,169, Mar. 25, 2025.

(Continued)

*Primary Examiner* — Thomas D Lee
(74) *Attorney, Agent, or Firm* — Own Innovation; Daniel Biggs; James W. Hinton

(57) ABSTRACT

The invention relates to systems and methods for predicting ischemic brain tissue fate from multi-phase CT-angiography. More specifically, systems and methods are provided that enable meaningful prediction of core, penumbra and perfusion from mCTA images using software that has been trained via machine learning to interpret mCTA images.

24 Claims, 25 Drawing Sheets

Related U.S. Application Data

(60) Provisional application No. 62/987,448, filed on Mar. 10, 2020.

(51) Int. Cl.
| | |
|---|---|
| *G06T 7/00* | (2017.01) |
| *G16H 50/50* | (2018.01) |
| *G16H 50/70* | (2018.01) |

(52) U.S. Cl.
CPC .......... *A61B 6/5247* (2013.01); *G06T 7/0016* (2013.01); *G16H 50/50* (2018.01); *G16H 50/70* (2018.01); *G06T 2200/24* (2013.01); *G06T 2207/10081* (2013.01); *G06T 2207/10088* (2013.01); *G06T 2207/20081* (2013.01); *G06T 2207/30016* (2013.01); *G06T 2207/30104* (2013.01)

(56) References Cited

U.S. PATENT DOCUMENTS

| | | | |
|---|---|---|---|
| 2019/0274652 A1 | 9/2019 | Goyal et al. | |
| 2019/0304606 A1 | 10/2019 | Menon et al. | |

FOREIGN PATENT DOCUMENTS

| | | |
|---|---|---|
| WO | 2014036638 A1 | 3/2014 |
| WO | 2016001825 A1 | 1/2016 |
| WO | 2020154398 A1 | 7/2020 |

OTHER PUBLICATIONS

European Patent Office, Extended European Search Report for EP Application No. 21768629.4, Jul. 3, 2024.

Nannoni et al., "Collaterals are a major determinant of the core but not the penumbra volume in acute ischemic stroke", Neuroradiology, May 23, 2019, pp. 971-978, 61.

Wannamaker et al, "Multimodal CT in Acute Stroke", Current Neurology and Neuroscience Reports, Jul. 27, 2019, 19:63.

Albers, Gregory W., et al.; "Thrombectomy for Stroke at 6 to 16 Hours with Selection by Perfusion Imaging"; New England Journal of Medicine, vol. 378, No. 8; Massachusetts Medical Society; Feb. 22, 2018; 11 Pages.

Almekhlafi, M.A., et al.; "Imaging Triage of Patients with Late-Window (6-24 Hours) Acute Ischemic Stroke a Comparative Study Using Multiphase CT Angiography versus CT Perfusion"; Observational Study, American Journal of Neuroradiology (AJNR), vol. 41, 1; Jan. 1, 2020; 5 Pages.

Boers, Anna M. M., et al.; "Association of follow-up infarct volume with functional outcome in acute ischemic stroke: a pooled analysis of seven randomized trials"; Journal of Neurointerventional Surgery, vol. 10, No. 12; Dec. 2018; 6 Pages.

Boutelier, Timothé, et al.; Bayesian Hemodynamic Parameter, Estimation by Bolus Tracking Perfusion Weighted Imaging; IEEE Transactions on Medical Imaging, vol. 31, No. 7; Jul. 2012; 15 Pages.

Campbell, Bruce C.V., et al.; "Cerebral Blood Flow Is the Optimal CT Perfusion Parameter for Assessing Infarct Core"; Stroke, Journal of the American Heart Association (JAHA), vol. 42, Issue 12; American Heart Association, Inc.; Dec. 2011; 6 Pages.

Campbell, Bruce C.V., et al.; "Endovascular Therapy for Ischemic Stroke with Perfusion-Imaging Selection"; New England Journal of Medicine, vol. 372, Issue 11; Massachusetts Medical Society; Mar. 12, 2015; 10 Pages.

Clèrigues, Albert, et al.; "Acute ischemic stroke lesion core segmentation in CT perfusion images using fully convolutional neural networks"; Computers in Biology and Medicine, vol. 115; Science Direct; Oct. 9, 2019; 7 Pages.

D'Esterre, Christopher D., et al.; "Time-Dependent Computed Tomographic Perfusion Thresholds for Patients With Acute Ischemic Stroke"; Stroke, Journal of the American Heart Association (JAHA), vol. 46, Issue 12; American Heart Association, Inc.; Dec. 2015; 8 Pages.

D'Esterre, Christopher D., et al.; "Regional Comparison of Multiphase Computed Tomographic Angiography and Computed Tomographic Perfusion for Prediction of Tissue Fate in Ischemic Stroke"; Stroke, AHA Journals, vol. 48, No. 4; Mar. 14, 2017; 7 Pages.

Demeestere, Jelle, et al.; "Review of Perfusion Imaging in Acute Ischemic Stroke: From Time to Tissue"; Stroke, AHA Journals, vol. 51, Issue 3; Feb. 3, 2020; 8 Pages.

Dundamadappa, S., et al.; "Multiphase CT Angiography a Useful Technique in Acute Stroke Imaging-Collaterals and Beyond"; American Journal of Neuroradiology (AJNR), vol. 42, No. 2; Feb. 1, 2021; 7 Pages.

Fahmi, Fahmi, et al.; "3D movement correction of CT brain perfusion image data of patients with acute ischemic stroke"; Neuroradiology, vol. 56, No. 6; Jun. 2014; 8 Pages.

Goyal, Mayank, et al.; "Randomized Assessment of Rapid Endovascular Treatment of Ischemic Stroke"; The New England Journal of Medicine, vol. 372, Feb. 11, 2015; 12 Pages.

Hoving, Jan W., et al.; "Volumetric and Spatial Accuracy of Computed Tomography Perfusion Estimated Ischemic Core Volume in Patients with Acute Ischemic Stroke"; Stroke, AHA Journals, vol. 49, Issue 10; Oct. 2018; 8 Pages.

Johnson, John A., et al.; "A model for capillary exchange"; American Journal of Physiology-Legacy Content, vol. 210, No. 6; Jun. 1, 1966; 5 Pages.

Kemmling, André, et al.; "Multivariate dynamic prediction of ischemic infarction and tissue salvage as a function of time and degree of recanalization"; Journal of Cerebral Blood Flow & Metabolism, vol. 35, No. 9; Jul. 8, 2015; 9 Pages.

Kudo, Kohsuke, et al.; "Differences in CT Perfusion Maps Generated by Different Commercial Software: Quantitative Analysis by Using Identical Source Data of Acute Stroke Patients"; Radiology, vol. 254, No. 1; Jan. 2010; 10 Pages.

Lee, Seong-Joon, et al.; "Optimal Multiphase Computed Tomographic Angiography-Based Infarct Core Estimations for Acute Ischemic Stroke"; Scientific Reports, vol. 9, No. 1; Oct. 23, 2019; 7 Pages.

Meijs, Midas, et al.; "Analysis of Perfusion MRI in Stroke: To Deconvolve, or not to Deconvolve"; Magnetic Resonance in Medicine 76; Wiley Periodicals; Oct. 2016; 9 Pages.

Menon, Bijoy K., et al.; "Association of Clinical, Imaging, and Thrombus Characteristics with Recanalization of Visible Intracranial Occlusion in Patients with Acute Ischemic Stroke"; JAMA Network, vol. 320, No. 10; Sep. 11, 2018; 10 Pages.

Menon, Bijoy K., et al.; "Multiphase CT Angiography: A New Tool for the Imaging Triage of Patients with Acute Ischemic Stroke"; RSNA Radiology Journals, vol. 275, No. 2; Jan. 29, 2015; 11 Pages.

Modat, Mark, et al.; "Fast free-form deformation using graphics processing units"; Computer Methods and Programs in Biomedicine, vol. 98, Issue 3; Elsevier, Science Direct; Jun. 2010; 7 Pages.

Mokin, Maxim, et al.; Predictive Value of RAPID Assessed Perfusion Thresholds on Final Infarct Volume in SWIFT PRIME (Solitaire With the Intention for Thrombectomy as Primary Endovascular Treatment); Stroke, Journal of the American Heart Association (JAHA), vol. 48, Issue 4; American Heart Association, Inc.; Apr. 2017; 7 Pages.

Najm, Mohamed, et al.; "Automated brain extraction from head CT and CTA images using convex optimization with shape propagation"; Computer Methods and Programs in Biomedicine, vol. 176; Elsevier, Science Direct; Jul. 2019; 8 Pages.

Nogueira, Raul G., et al.; "Thrombectomy 6 to 24 Hours after Stroke with a Mismatch between Deficit and Infarct"; New England Journal of Medicine, vol. 378, No. 1; Massachusetts Medical Society; Jan. 4, 2018; 11 Pages.

Ospel, J.M., et al.; "Displaying Multiphase CT Angiography Using a Time-Variant Color Map: Practical Considerations and Potential Applications in Patients with Acute Stroke"; AJNR American Journal of Neuroradiology, vol. 41. No. 2; Feb. 2020; 6 Pages.

(56)             References Cited

OTHER PUBLICATIONS

Qiu, Wu, et al.; "Confirmatory Study of Time-Dependent Computed Tomographic Perfusion Thresholds for Use in Acute Ischemic Stroke"; Stroke, AHA Journals, vol. 50, Issue 11; Nov. 2019; 5 Pages.

Qiu, Wu, et al.; "Letter to Editor: Response to Confirmatory Study of Time-Dependent Computed Tomographic Perfusion Thresholds for Use in Acute Ischemic Stroke"; Stroke, AHA Journals, vol. 51, Issue 1; Jan. 2020; 1 Page.

Reid, Meaghan, et al.; "Accuracy and Reliability of Multiphase CTA Perfusion for Identifying Ischemic Core"; Clinical Neuroradiology, vol. 29; Springer Nature, Switzerland; Aug. 21, 2018; 10 Pages.

Rocha, Marcelo, et al; "Fast Versus Slow Progressors of Infarct Growth in Large Vessel Occlusion Stroke: Clinical and Research Implications"; Stroke, AHA Journals, vol. 48, Issue 9; Sep. 2017; 7 Pages.

Stewart, Errol E., et al.; "Correlation Between Hepatic Tumor Blood Flow and Glucose Utilization in a Rabbit Liver Tumor Model"; RSNA Radiology Journals, vol. 239, No. 3; 2006; 11 Pages.

Yu, Amy Y. X., et al.; "Multiphase CT angiography increases detection of anterior circulation intracranial occlusion"; American Academy of Neurology, vol. 87, No. 6; Jul. 6, 2016; 8 Pages.

Yu, Inwu, et al.; "Admission Diffusion-Weighted Imaging Lesion Volume in Patients with Large Vessel Occlusion Stroke and Alberta Stroke Program Early CT Score of ≥6 Points: Serial Computed Tomography-Magnetic Resonance Imaging Collateral Measurements"; Stroke, AHA Journals, vol. 50, Issue 11; Sep. 26, 2019; 6 Pages.

Zussman, Benjamin M., et al.; "The Relative Effect of Vendor Variability in CT Perfusion Results: A Method Comparison Study"; AJR American Journal of Roentgenology, vol. 197, No. 2; Aug. 2011; 6 Pages.

International Search Report and Written Opinion of the International Searching Authority; Application No. PCT/CA2021/050320; Completed: May 3, 2021; Mailing Date: May 17, 2021; 14 Pages.

\* cited by examiner

Impulse residual function calculated from deconvolution algorithm in CTP software Training and Testing strategy of machine learning models to predict ischemic infarct, penumbra and perfusion status (a) Derivation and testing of Penumbra model and Infarction model using follow up infarct as reference standard (b) Derivation and testing of Perfusion model using time-dependent Tmax thresholded map as reference standard Training and testing each of three machine learning models Case 1: 83 years old, female, stroke onset to CT time: 95 mins, left ICA occlusion, NIHSS 23, ASPECTS 10

Contour Color Code:
inner or single contour "Red" R (core);
outer contour- "Blue" B (penumbra)
All areas within a red contour are red. All areas
between a red contour and blue contour are blue.

Machine learning prediction using mCTA

CTP prediction

Reference Standard

Case 2: 87 years old, male, stroke onset to CT time: 208 mins, left distal M1 occlusion, NIHSS 28, ASPECTS 5

Non contrast CT scan is unremarkable

SYSTEM AND METHODS OF PREDICTION OF ISCHEMIC BRAIN TISSUE FATE FROM MULTI-PHASE CT-ANGIOGRAPHY IN PATIENTS WITH ACUTE ISCHEMIC STROKE USING MACHINE LEARNING

TECHNICAL FIELD

The invention relates to systems and methods for predicting ischemic brain tissue fate from multi-phase CT-angiography (mCTA). More specifically, systems and methods are described that enable meaningful prediction of core, penumbra and perfusion from mCTA images using software that has been trained via machine learning to interpret mCTA images.

BACKGROUND

Ischemic stroke is an acute disease where tissue death (infarction) within the brain of different patients will progress at different rates from the time of the ischemic event. The rate of infarction within a patient depends on a large number of physiological factors.

For the physician diagnosing and treating ischemic strokes, when a stroke patient arrives at a hospital, it is very important for the physician to obtain as much knowledge about the nature of the stroke as soon as possible in order to make an effective diagnosis and effective decisions regarding treatment. As is readily understood, time to effect diagnosis and treatment is very important as faster diagnoses will impact treatment decisions and can minimize the amount of brain tissue that is ultimately affected as a result of the stroke.

For example, in the case of an ischemic stroke, it is important for the physician to know where the vessel occlusion is, how big the occlusion is, where any unsalvageable brain tissue ("core") is and, how big and where is the brain tissue that may have been affected by the ischemic event but that may potentially be saved ("penumbra").

More specifically, the penumbra is tissue around the ischemic event that can potentially stay alive for a number of hours after the event due to perfusion of this tissue by collateral arteries that may be providing sufficient blood and oxygen to prevent this tissue from dying for a period of time.

When the physician has good information about the collaterals and how the collaterals may be located in and around the penumbra, treatment decisions can be made that can significantly affect patient outcomes.

In an emergency or acute situation, the process of making a decision will consider the amount of information at a given moment in time. That is, a definitive 'yes' decision can be made to take action or a 'no' decision can be made to take no action based on the current information. In addition, a third decision choice can be to wait for additional information. In the situation of acute stroke (and other emergency scenarios), time to make a definitive diagnostic/treatment decision must be balanced against the likelihood of a negative outcome that results simply from the delay in making a decision. In other words, the decision to wait for more information must consider what the effects of a delay in making a decision might be.

At the present time, in many treatment centers, when a stroke patient arrives, the assessment protocol is generally as follows:

a. Conduct a CT scan of the head to rule out or look for evidence of a hemorrhagic stroke.

b. Conduct a CT angiogram (CTA) to locate the site of vessel occlusion.

c. Conduct a CT perfusion (CTP) study to create perfusion maps that provide the physician with information about various parameters including cerebral blood flow, cerebral blood volume and mean transit time.

An alternative to a CTP perfusion study is to conduct a "multi-phase" CT angiogram (mCTA) study. An mCTA study differs from a CTP study in that significantly fewer images are taken compared to a CTP study but sufficient to make legitimate diagnosis/treatment decisions. As such, mCTA studies can be advantaged over CTP studies as they can be undertaken more rapidly with less radiation exposure to the patient.

As is known, each of these generalized steps will be affected by a large number of factors and the time to complete each of them will be variable from patient to patient and between different treatment centers. For example, such factors may include resource availability (e.g., trained medical staff and equipment) as well as processing times required by CT scan equipment and other ancillary hardware and software to present data to physicians.

For the purposes of illustration, these factors are described in terms of a representative diagnosis and treatment scenario of a patient exhibiting symptoms of a stroke, the patient arriving at the emergency room of a treatment center and who thereafter receives the above CT procedures as part of the diagnostic protocol. Table summarizes a number of the key process steps and typical times that may be required to complete each step and are discussed below.

TABLE 1

| Typical Diagnostic Steps and Completion Times | | | |
|---|---|---|---|
| Procedure | Time (minutes) | Elapsed Total | Comments |
| Initial Assessment | 3-5 | 3-5 | |
| Transfer and Preparation for CT Scan | 20 | 23-25 | |
| CT Scan | 1 | 24-26 | |
| CT Scan Interpretation and CT Angiogram Preparation | 2-3 | 26-30 | CT Angiogram Preparation may be concurrent with CT Scan Interpretation |
| CT Angiogram Procedure | 1-3 | 27-33 | |
| CT Angiogram Post Processing | 2 | 29-35 | |
| CT Angiogram Interpretation and CT Perfusion Preparation | 4 (minimum) | 33-39 | CT Perfusion Preparation may be concurrent with CT Scan Interpretation |
| CT Perfusion Procedure | 1 | 34-40 | |
| CT Perfusion Post Processing | Variable 2-10 (minimum) | 36-50 | Will depend on vendor specifics |
| CT Perfusion Interpretation | Variable 2-10 (minimum) | 38-60 | Will depend factors including: time of day; center; vendor equipment etc. |

Upon arrival at the treatment center, an emergency room physician conducts a preliminary assessment of the patient. If the preliminary assessment concludes a potential stroke, the patient is prepared for a CT scan. The time taken to initially assess a potential stroke patient upon arrival at the treatment facility may be 3-5 minutes.

Preparing the patient for a CT scan involves a number of steps including transferring the patient to the CT imaging suite and connecting an intra-venous line to the patient to enable the injection of contrast agent into the patient during the various CT procedures.

The CT scan includes conducting an x-ray scan of the patient together with a computerized analysis of the x-ray data collected. More specifically, as is known, during a CT scan, beams of x-rays are emitted from a rotating device through the area of interest in the patient's body from several different angles to receivers located on the opposite sides of the body. The received data is used to create projection images, which are then assembled by computer into a two or a three-dimensional picture of the area being studied. More specifically, the computer receives the x-ray information and uses it to create multiple individual images or slices which are displayed to the physician for examination.

CT scans require that the patient hold still during the scan because significant movement of the patient will cause blurred images. This is sometimes difficult in stroke patients and hence sometimes head restraints are used to help the patient hold still. Complete scans take only a few minutes.

Upon completion of the initial CT scan including the post-processing time to assemble the images, the physician interprets the images to determine a) if a stroke has occurred and, b) if so, to determine if the stroke is hemorrhagic or ischemic. If the stroke is hemorrhagic, different procedures may be followed. It will typically take the physician in the order of 1-2 minutes from the time the images are available to make the determination that the stroke is hemorrhagic or ischemic.

If the stroke is ischemic, the decision may be made to conduct a CT angiogram (CTA).

CT angiography procedures generally require that contrast agents be introduced into the body before the scan is started. Contrast is used to highlight specific areas inside the body, in this case the blood vessels. In addition, because of presence of contrast in the very small vessels of the brain, overall, the brain looks brighter (has a higher Hounsfield value) also known as contrast enhancement. Contrast agents are iodine-based compounds that inhibit the passage of x-rays through the tissue. As such, they can be effective in enhancing the distinction between tissues where the contrast agent is present compared to those tissues where it is not. The CT angiogram requires additional preparation time but will typically not require that the patient be moved. Generally, CT angiogram procedures involve the injection of a bolus of contrast through an IV line followed by the CT scan. A typical contrast bolus may be 70-100 ml injected at 5 ml/second. The volume and injection rate of contrast is determined by the procedure being followed and is generally injected in a minimally sufficient volume to be present in the tissues of interest at the time the CT scan is conducted. Over a relatively short time period, the contrast becomes diffused within the body thereby providing only a relatively short window of time to conduct a CT procedure.

The CT angiogram data is substantially greater than what is collected from a basic scan and like a basic CT scan must be subjected to post-processing to create the images. The post-processing time is typically in the range of 2-5 minutes.

After processing, the physician interprets the data and makes a decision regarding treatment. Generally, the physician is looking to determine a) where is the occlusion? b) what is the size of the core? and c) obtain a qualitative feel for penumbra and collaterals.

Ultimately, and based on these factors, the physician is looking to make a decision on what brain tissue is worth fighting for. In other words, based on the combination of all these factors, the physician is looking to decide either that very little, or no penumbra can be saved, or alternatively that it appears that penumbra can be saved and it is worthwhile to do so.

The CT angiogram provides relatively little data about collaterals and perfusion to the ischemic tissue as it is only a picture of the brain at one instance in time. That is, as it takes time for contrast agent to flow through the brain tissues and such flow will be very dependent on the ability of vessels to carry the contrast agent, a single snapshot in time does not give the physician enough information to make a diagnostic and/or treatment decision. Hence, CT perfusion (CTP) procedures/studies may be undertaken to give the physician a more qualitative and quantitative sense of brain perfusion. Like CT angiogram, CT perfusion procedures involve the injection of contrast agent into the patient. It should also be noted that some centers may choose to do a CT perfusion study before the CT angiogram because they feel that the contrast injection from the CT angiogram interferes with the quality of data of the CT perfusion.

Perfusion computed tomography (CTP) allows qualitative and quantitative evaluation of cerebral perfusion by generating maps of various parameters including cerebral blood flow (CBF), cerebral blood volume (CBV), and mean transit time (MTT). The technique is based on the central volume principle (CBF=CBV/MTT) and requires the use of complex software employing complex deconvolution algorithms to produce perfusion maps. Other maps such as Tmax maps may also be created.

CTP studies are acquired with repeated imaging through the brain while the contrast is injected. The technique varies significantly from vendor to vendor and also from center to center, relies on certain physiological assumptions that are not always valid and hence requires specialized training with the specific equipment at each center. CTP typically involves imaging of the brain over approximately 60-70 seconds (at 1-4 second intervals) in order to acquire multiple images. The technique is quite vulnerable to patient motion and also requires the patient to hold still for the period. Furthermore, CTP also involves substantial radiation exposure in the range of 3.5-5 mSv as the number of images taken over the time period is significant.

The procedure generates a large dataset that must then be transferred to a dedicated workstation for post-processing. This step may take over 3-5 minutes in order to produce separate maps of each of CBF, CBV, and MTT. The perfusion maps are typically color-coded maps.

Importantly, the post-processing requires the use of specialized and very often proprietary software that must be run by trained individuals. Ultimately, the time taken to fully complete CTP acquisition and analysis is highly variable as the above factors including the vendor, the speed of data transfer, local expertise, the time of day the study is being undertaken (i.e., working hours vs. after hours) as well as other factors can all have an effect on the actual amount of time required to complete the study.

Thus, while perfusion CT is not a perfect technique, it has been found to be useful for noninvasive diagnosis of cerebral ischemia and infarction as it does provide some degree of quantitative determination of core and penumbra. However, as noted above, there are problems with these procedures. In summary, these problems include:

a. CT perfusion takes time to complete (8-30+ minutes total).

b. Patient motion can affect results.

c. Significant post-processing time is required to complete a full perfusion map.

d. Additional radiation exposure to the patient e. Need for additional contrast agents.

f. Non-standardized procedures for completing the perfusion map.

g. Variations in technique with different vendor equipment.

h. Physiological assumptions that are not always valid.

i. Lack of consensus in the medical community regarding the interpretation and best practices for treatments based on the CT perfusion maps.

j. Lack of information regarding rate of infarct growth.

k. Significant variability across vendors for the degree of coverage of the brain (e.g., 4 to 16 cms). Also, some vendors have the option of covering 8 cm using a 'toggle table' technique that may introduce additional errors.

Multi-phase CTA (mCTA) has proven to be an effective alternative to CTP as a means of providing faster and usable information to enable a physician to make effective diagnosis and treatment decisions while subjecting the patient to lower amounts of radiation. However, under various imaging scenarios, there has been a need for additional information in addition to the mCTA images to improve the precision of diagnoses and ideally to improve the presentation of information to a physician and specifically enable the utilization of mCTA images to provide effective core, penumbra and perfusion maps from mCTA images.

Medium Vessel Occlusion

Medium vessel occlusion (MeVO) as compared to large vessel occlusion (LVO) and small vessel occlusion (SVO) is generally defined as occlusion of vessels distal to level 1 brain vessels and generally refers to occlusions within level 2 (approximate 2 mm diameter) and level 3 vessels (approximate 1 mm diameter). As is known, level 1 and level 2 vessels are generally referred by the relative location of these vessels with respect to a frontal plane including anterior (A), posterior (P) and middle (M) positions. Thus, for reference, A2 and A3 vessels are anterior level 2 and 3 vessels, M2 and M3 vessels are middle level 2 and 3 vessels and P2 and P3 vessels are posterior level 2 and 3 vessels (see FIG. 7).

As is known, the anatomy of brain vessels is such that with each bifurcation, the relative size of daughter vessels becomes smaller, and the volume of tissue perfused downstream of each bifurcation also becomes smaller. In addition, with each bifurcation to smaller vessels, the variability in anatomy between people becomes higher, the tortuosity of vessels becomes higher, and the total number of junctions and definable zones becomes higher within a larger region.

As a result, the ability to determine the location of MeVO becomes more difficult as the number of zones/areas where the MeVO may be substantially higher.

At present, MeVO (as compared to LVO or SVO) is diagnosed by the physician by carefully looking at the source images of the CT angiogram. Looking at the CTP maps can be of help. That is, if a zone of the brain is observed as having an affected area (penumbra and core) at a particular level(s) or zone as shown by the CTA images and/or CTP map, the physician will look to areas/zones proximal to that area/zone to determine which vessel may be occluded and is causing the affected tissue. In order to locate the occlusion, the problem is more difficult than with LVOs for the reasons outlined above and specifically because the number of potential zones is larger (with each zone also being smaller), the vessels are smaller, the anatomy is more variable, and the tortuosity of vessels may be greater. As such, the physician, based on their knowledge of brain anatomy will look for the specific vessel by examining raw contrast CTA images for particular zones proximal to the affected tissue that show evidence of contrast either being held up or having cleared. Factors including the location, size/volume, shape, confluence, involvement of the cortex and sub-cortical white matter, and knowledge of the known supply by vessels may be taken into consideration in determining whether an occlusion is an LVO, MeVO or SVO.

For example, it may be observed that a left frontal region of a particular size and shape just cranial to the Sylvian fissure is ischemic. It is then expected that that region is supplied by one of the branches of the anterior division of the MCA (anterior M2 or one of its branches). From this knowledge, the physician will look at images proximal to the hypoperfused region to locate and observe the vessels to determine where an occlusion may be. By observing the behavior of the contrast across different phases of images, the physician may observe that of 4 vessels in a zone, vessels 1, 2 and 4 are open whereas vessel 3 is occluded. Thus, from manually observing these vessels the site of the occlusion can be determined. Based on the size and location of the ischemic tissue, LVO is excluded.

This process can be quite time consuming and requires a high level of expertise that may not be available 24/7 at many centres and require time being spent moving backwards and forwards through images to trace a number of specific vessels to hunt for the single vessel that is occluded.

Accordingly, there has been a need for improved systems able to assist in the diagnosis of MeVO.

SUMMARY

In accordance with the invention, systems, and methods for predicting ischemic brain tissue fate from multi-phase CT-angiography (mCTA). More specifically, systems and methods are described that enable meaningful prediction of core, penumbra and perfusion from mCTA images using software that has been trained via machine learning to interpret mCTA images.

In a first aspect, a method of predicting any one of or a combination of core, penumbra and perfusion status in a stroke patient from a series of current multi-phase computed tomography (mCTA) images obtained from a current patient is described, the method including the steps of: within a database of historical data, the historical data having a plurality of historical images from patients having undergone computed tomography perfusion (CTP) study and non-contrast computed tomography (NCCT) and wherein the historical images have been previously analyzed to identify historical features of interest including an estimate of core, penumbra and perfusion status, i. analyzing the current mCTA images and identifying current features of interest wherein the current features of interest are determined by an analysis of density value, time and location from the current mCTA images; and, ii. comparing the current features of interest from step i against corresponding historical features of interest and fitting the current features of interest to the historical features of interest to predict any one of or a combination of core, penumbra and perfusion status in the current mCTA images. The mCTA images preferably include 3-5 phases of images.

In various embodiments, the method may also include the following features or steps:

The historical data includes treatment data associated with each patient including no reperfusion treatment or reperfusion treatment data pertaining to the historical images.

The database includes data analysis of follow-up non-contrast CT (NCCT) and/or diffusion weighted (DV) magnetic radiation imaging (MRI) of the historical images describing patient outcome.

The database includes data analysis of past mCTA studies from a second group of patients that have undergone mCTA and no perfusion treatment and follow-up non-contrast CT (NCCT) and/or diffusion weighted (DW) MRI.

The database includes data analysis of past-mCTA studies from a second group of patients that have undergone mCTA and perfusion treatment and follow-up non-contrast CT (NCCT) and/or diffusion weighted (DVW) MRI.

Steps i and ii are completed in 10 minutes or less after obtaining the current mCTA images.

The historical data includes data quantifying a patient's recovery status between full recovery to poor recovery.

The historical data includes any one of or a combination of a calculation of time to maximum (Tmax), cerebral blood volume (CBV) and cerebral blood flow (CBF) values from the historical images.

The method includes the step of quantifying a likelihood of success of conducting a reperfusion treatment based on a comparison of predicted core, penumbra and/or perfusion status in the current patient and actual outcome data from historical data.

In another aspect, a method of quantifying core and/or penumbra from a plurality of current multi-phase computed tomography (mCTA) images of a patient is described, the method including the steps of: introducing the plurality of mCTA images into a prediction model, the prediction model derived from historical computed tomography perfusion (CTP) image data and CTP study data that quantified Time to Maximum (Tmax), cerebral blood volume (CBV) and cerebral blood (CBF) from the historical CTP image data and wherein the prediction model fits the current mCTA images into the prediction model to predict core and/or penumbra from the current mCTA images.

In various embodiments, the method includes may also include the following features or steps:

The historical CTP image data further includes patient treatment data, patient post-treatment follow-up images and patient outcome data and where the prediction model fits a current patient core/penumbra prediction to the patient outcome data to obtain a prediction of outcome of the current patient.

The patient treatment data includes surgical procedure data whether undertaken or not.

The method includes the steps of calculating prediction maps and displaying the prediction maps on a display system and where the prediction maps include core and/or penumbra as core and/or penumbra prediction maps.

The method includes the steps of calculating an outcome score for a current patient based on a calculation of total core and/or penumbra and/or diffusion, fitting the total core and/or penumbra and/or diffusion to past patient data having outcome data and displaying the outcome score on a display system.

The method includes the steps of predicting core/penumbra within 10 minutes of initially obtaining current mCTA images.

In another aspect, a method of building and training a machine learning database to enable prediction of any one of or a combination of core, penumbra and perfusion status from multi-phase computed tomography (mCTA) images is described, comprising the steps of: i. introducing historical patient data into a database, the historical patient data including images from multiple computed tomography perfusion (CTP) studies and treatment follow-up images; ii. analyzing the historical patient data to extract features of interest relating to occlusion location, core, penumbra and perfusion; iii. introducing historical mCTA patient data in the database, the historical mCTA patient data including multiple sets of mCTA images and testing the sets of mCTA images obtained in step i using a machine-learning algorithm, where each set of mCTA images include phases of images and follow-up images; iv. deriving a classifier prediction model from step iii; and, v. introducing a single set of mCTA image data into the prediction model from step iv and analyzing the mCTA image data to produce any one of or a combination of a core, penumbra and status prediction probability map for the mCTA image data.

In various embodiments, the method includes the following features or steps:

The historical patient data includes data from patients having undergone reperfusion and patients not having undergone reperfusion.

The historical mCTA patient data includes data from patients having undergone reperfusion and patients not having undergone reperfusion.

The prediction model calculates predicted core volume.

The prediction model calculates predicted penumbra volume.

The prediction model calculates predicted tissue perfusion status.

The prediction model determines follow-up infarct volume and utilizes the follow-up infarct volume as a reference standard for step v.

The step of feature extraction includes the steps of analyzing density and acquisition time of features.

Density and acquisition time analysis includes for each voxel:

calculating average and standard deviation of Hounsfield Units (HU) across each phase of mCTA images;

calculating a coefficient of variance of HUs for each phase of mCTA images;

calculating slopes of HUs between any two phases of mCTA images;

determining peak of HUs across the phases of mCTA images; and, determining a time peak of HUs.

The features are calculated in the neighborhood centered at each voxel at different scales.

The method includes the step of comparing the mCTA prediction probability map against follow-up images to test the accuracy of the model.

In another aspect, a method is described, comprising the steps of: accessing, at one or more computing devices, a plurality of multi-phase computed tomography angiogram (mCTA) images from a current patient; determining using an image classification engine whether the accessed image includes any one of or a combination of core or penumbra, wherein the image classification engine has been trained, using unsupervised learning, to estimate from the mCTA images a quantity of core and penumbra; and, displaying via a graphical user interface a graphical representation of the quantity of core and/or penumbra. The method may include a step of estimating and displaying perfusion status.

In another aspect, a method of building and training a machine learning database and model to enable prediction of any one of or a combination of core, penumbra and perfusion status from sets of multi-phase computed tomography (mCTA) images and sets of computed tomography perfusion (CTP) images is described, where each set of mCTA images include phases of images and follow-up images, the method including the steps of: i. introducing historical patient mCTA and CTP images into a database and analyzing the mCTA and CTP images to extract features of interest relating to occlusion location, core, penumbra and perfusion; ii. testing multiple sets of mCTA images against patterns obtained in step i using a machine-learning algorithm; deriving a classifier prediction model from step ii; iii. introducing a single set of mCTA image data into the prediction model from step iii and analyzing the mCTA image data to produce any one of or a combination of a core, penumbra and perfusion status prediction probability map for the mCTA image data; and, iv. comparing the mCTA prediction probability map against follow-up images to ascertain the accuracy of the model.

In various embodiments, the method may also include the following features or steps:

Steps ii and iii includes two-stage training including a first penumbra stage that derives a penumbra area and a second core stage that derives a core area.

The machine learning model comprises one of a random forest, a support vector machine, a neural network, or a k nearest neighbor model.

The features of interest relating to occlusion location, core, penumbra and perfusion, are identified by any one of or a combination of first-order statistics including mean and histogram of HU values, and texture features including gray-level co-occurrence matrix and gray level run length matrix.

The features of interest relating to occlusion location, core, penumbra and perfusion are calculated at different scales for a given voxel corresponding to the axial imaging and where the features of interest are calculated at low, median, and high-resolution scales.

The features of interest contributing to occlusion location, core, penumbra and perfusion are automatically selected using a feature selection module utilizing any one of or a combination of univariate selection, feature importance, and correlation matrix with heatmap.

The at least one probability map is thresholded to generate infarct core and/or penumbra and/or perfusion volume for an axial imaging slice.

Morphological operations including dilation and/or erosion and component analysis are applied after thresholding to remove isolated islands.

The model enables prediction of any one of or a combination of core and penumbra within a multiple label machine learning model including a core label, penumbra label and normal tissue label.

The method includes the step of inputting historical patient meta data including age, sex, NIHSS, ASPECTS, and occlusion site.

In another aspect, a method of predicting a plurality of contrast enhanced volumes in a brain scan image is described including the steps of: from a series of multi-phase computed tomography (mCTA) images from a stroke patient and a plurality of historical images from patients having undergone non-contrast computed tomography (NCCT) and computed tomography perfusion (CTP) study, comparing signal intensity fluctuations of voxel data of the mCTA images against corresponding voxels from the historical CTP images and time synchronizing a plurality of mCTA volumes to a plurality of CTP volumes; from time synchronized mCTA and historical CTP volumes, comparing corresponding voxels from the mCTA images and historical CTP images and finding at least one match of historical CTP images; and, utilizing the at least one match of historical CTP images as basis for predicting a contrast enhanced volume for the mCTA images. The method may include the step of building and displaying at least one predictive map showing a combination of core and penumbra and/or perfusion.

In another aspect, a method of deriving and presenting information useful in diagnosing medium vessel occlusion (MeVO) in a current patient is described including the steps of: from a plurality of CT images showing hypoperfused regions of the current patient; i. quantifying a hypoperfused tissue volume in the current patient; ii. comparing the hypoperfused tissue volume from step i to threshold volume parameters defining a MeVO event and determining if the hypoperfused tissue matches volume parameters of a MeVO event; and, iii. if a MeVO event is determined, display a MeVO event determination.

In various embodiments, the method may also include the following features or steps:

Steps i and ii include quantifying a hypoperfused tissue shape in the current patient and comparing the hypoperfused tissue shape to threshold shape parameters defining a MeVO event and determining if the hypoperfused tissue shape matches shape parameters of a MeVO event.

Steps i and ii include quantifying a hypoperfused tissue location in the current patient and comparing the hypoperfused tissue location to threshold location parameters defining a MeVO event and determining if the hypoperfused tissue location matches location parameters of a MeVO event.

Steps i and ii include quantifying involved cortex.

Steps i and ii include quantifying hypoperfused tissue confluence in the current patient and comparing the hypoperfused tissue confluence to hypoperfused tissue confluence parameters defining a MeVO event and determining if the hypoperfused tissue confluence matches hypoperfused tissue confluence of a MeVO event.

The method further includes the steps of correlating the hypoperfused tissue location to corresponding hypoperfused locations from historical patient data wherein historical patient data includes data marking past MeVO events; and determining a best fit of historical patient image data and marking current patient images with MeVO location data derived from the historical patient image data.

The historical patient data with past MeVO events includes data quantifying proximal voxel location relevant to a past MeVO event within a past patient record.

Historical patient data records have been previously analyzed to derive 2D and/or 3D relationships between level 1-3 vessels.

Historical patient data records have been previously analyzed to define volumes of tissue as level 1, level 2 or level 3 tissue and wherein each volume of level 1, level 2 or level 3 tissue has at least one, equal, distal or proximal relationship with an adjacent volume of tissue.

The method includes the step of, after step iii, examining changes in contrast densities in adjacent proximal volumes across two or more phases of CTA images for the current patient and based on those changes marking changes in contrast density as normal flow or abnormal flow.

The method includes the step of discarding volumes showing normal flow from further analysis.

The method includes the step of utilizing volumes showing normal flow as a baseline for contrast density analysis.

The method includes the step of marking volumes showing abnormal flow for further analysis.

The method includes the step of analyzing zones where contrast abruptly transitions from no contrast to significant contrast between adjacent images or vice versa to identify vessels of interest.

The method includes the step of marking and displaying zones where contrast abruptly transitions on CTA images of the current patient.

The method includes the steps of providing at least one output selected from any one of or a combination of a) presence or not of MeVO; b) zone of interest marking and c) vessel of interest.

In another aspect, a method of deriving and presenting information useful in diagnosing medium vessel occlusion (MeVO) in a current patient is described, comprising the steps of from a plurality of CT images showing at least one hypoperfused region of the current patient; i. identifying the at least one hypoperfused region and correlating the at least one hypoperfused regions to one or more corresponding hypoperfused regions from within historical patient data; and, ii. deriving and identifying immediately proximal vessels/zones in the current patient based on best match(s) to the historical patient data and marking the proximal vessel/zones as predicted MeVO locations on current patient CT images.

In various embodiments, the method includes the following features or steps:

The method includes the steps of quantifying a hypoperfused tissue shape in the current patient and comparing the hypoperfused tissue shape to threshold shape parameters defining a MeVO event and determining if the hypoperfused tissue shape matches shape parameters of a MeVO event.

The method includes the steps of quantifying a hypoperfused tissue location in the current patient and comparing the hypoperfused tissue location to threshold location parameters defining a MeVO event and determining if the hypoperfused tissue location matches location parameters of a MeVO event.

The method includes the steps of quantifying involved cortex.

The method includes the steps of quantifying hypoperfused tissue confluence in the current patient and comparing the hypoperfused tissue confluence to hypoperfused tissue confluence parameters defining a MeVO event and determining if the hypoperfused tissue confluence matches hypoperfused tissue confluence of a MeVO event.

The method includes the steps of correlating the hypoperfused tissue location to corresponding hypoperfused locations from historical patient data wherein historical patient data includes data marking past MeVO events; determining a best fit of historical patient image data and marking current patient images with MeVO location data derived from the historical patient image data.

The historical patient data with past MeVO events includes data quantifying proximal voxel location relevant to a past MeVO event within a past patient record.

BRIEF DESCRIPTION OF THE DRAWINGS

Various objects, features and advantages of the invention will be apparent from the following description of particular embodiments of the invention, as illustrated in the accompanying drawings. The drawings are not necessarily to scale, emphasis instead being placed upon illustrating the principles of various embodiments of the invention.

Similar reference numerals indicate similar components.

FIG. 7A shows an unremarkable non-contrast CT scan in a patient having an acute stroke with aphasia; FIG. 7B shows the area of the brain that is hypoperfused resulting in the patients symptoms; the map could be created using an mCTA prediction map; FIG. 7C shows a zone of interest predicted using the MeVO tool; FIG. 7D shows identification of a particular vessel of interest following further processing with the MeVO tool; FIG. 7E shows vessel occlusion from conventional angiography; FIG. 7F shows a follow-up image following successful reperfusion; FIG. 7G is a flowchart outlining a process of providing useful information to a physician diagnosing MeVO in accordance with one embodiment of the invention; and FIG. 7H shows a representative 2D and partial 3D map of the relationship of L1-L3 voxels.

DETAILED DESCRIPTION OF THE INVENTION

Figure 1:
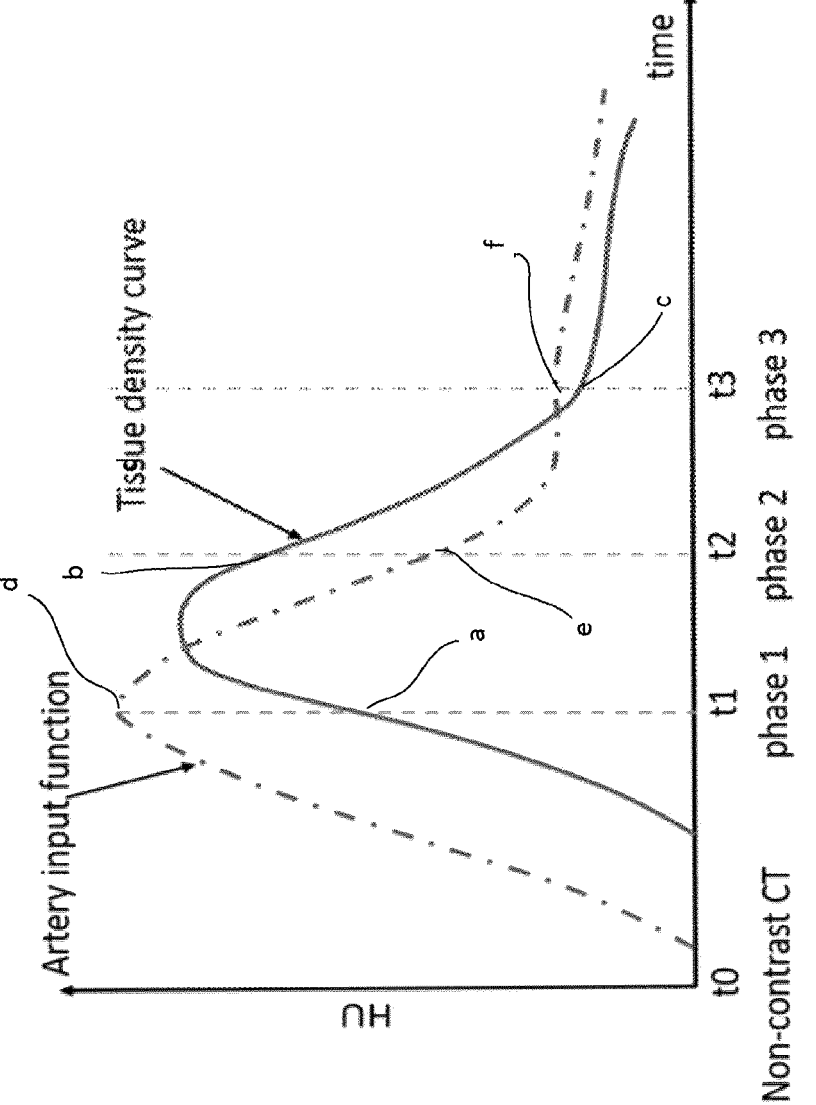
FIG. 1 is a graph showing typical time density curves and acquisition of mCTA images.

With reference to the figures, systems, and methods for predicting ischemic brain tissue fate from multi-phase CT-angiography (mCTA) are described. More specifically, systems and methods are described that enable meaningful prediction of core, penumbra and perfusion from mCTA images using software that has been trained via machine learning to interpret mCTA images.

Terms used herein have definitions that are reasonably inferable from the drawings and description.

Introduction

Various aspects of the invention will now be described with reference to the figures. For the purposes of illustration, components depicted in the figures are not necessarily drawn to scale. Instead, emphasis is placed on highlighting the various contributions of the components to the functionality of various aspects of the invention. A number of possible alternative features are introduced during the course of this description. It is to be understood that, according to the knowledge and judgment of persons skilled in the art, such alternative features may be substituted in various combinations to arrive at different embodiments of the present invention.

A primary objective is to obtain from a relatively small number of mCTA images (typically 3-phases of CTA images), a meaningful prediction of core, penumbra and perfusion using a methodology and software that has been trained to interpret mCTA images.

As noted above, mCTA does not have the granularity of data that a CTP study provides. Hence, without additional boundaries and/or knowledge to interpret the mCTA data, the mCTA images are, on their own, not effective in accurately quantifying core, penumbra and perfusion.

Data Used in Building a Prediction Model

The inventors have determined that by using image data from past CTP studies, and specifically from a first groups of patients that have undergone:

a. CTP and no reperfusion treatment,
  b. CTP and reperfusion treatment, and
  c. follow-up Non-Contrast CT (NCCT)/Diffusion weighted (DW) MRI, as well as image data from past mCTA studies from a second group of patients that have undergone:

d. mCTA and no perfusion treatment,
  e. mCTA and reperfusion treatment; and,
  f. follow-up Non-Contrast CT (NCCT)/Diffusion weighted (DV) MRI, a database of scenarios that shows the "start to finish" outcomes for these groups of patients can be utilized to build and test prediction models.

In accordance with the invention, models have been developed and trained with the objective of being able to interpret current mCTA images in a clinical setting to create clinically meaningful core, penumbra and perfusion maps at the time treatment decisions are being made.

For background, an ischemic stroke patient that has gone through a CTP and/or mCTA diagnosis and treatment protocol may have an outcome that is anywhere between a full recovery (no core) or poor recovery (significant core). This same patient may have been subjected to either a reperfusion treatment or no reperfusion treatment.

It has been determined that by studying the diagnostic and follow-up images of a number of these patients, patterns of effects can be observed across the population. For example, past data from a patient cohort (eg. 40 patients having an M1 occlusion) having undergone CTP and follow-up studies, the CTP studies will have determined a range of Tmax, CBV and CBF values that enabled CTP maps to be created that showed core, penumbra and perfusion predictions for these patients. These patients will have undergone (or not) treatments as well as follow-up imaging that verifies an outcome. Similarly, for a different patient cohort, mCTA studies have been used to make treatment decisions. Again, treatments will have been undertaken (or not) as well as follow-up imaging that verifies an outcome.

By using this data from past patients within models and training the models to interpret past mCTA images, it has been determined that at the time of diagnosis and the time that treatment decisions are being made with a current patient, these models can be utilized to fit mCTA data within the models to create predictive maps (like those obtained by CTP) that can be utilized by the physician to give an idea of the likelihood of success of a treatment. For example, a decision to treat or not to treat may be made given the relative likelihood of success based on a predicted core/penumbra and/or perfusion status.

Building and Testing the Prediction Models

In this invention, mCTA images were analyzed against the boundaries defined by the above databases using machine learning procedures. As noted above, mCTA images are effective in diagnosing and making treatment decisions; however, until now have been unable to be used as tools to quantitatively predict core, penumbra and perfusion status.

Thus, the models sought to determine if information from mCTA images can be correlated to data from CTP studies, be then used to create core/penumbra/perfusion maps (ostensibly at the time of diagnosis and treatment decision) and then based on follow-up images demonstrated that the prediction maps correlated well to the final outcome as determined by final outcome images.

The models were built based on knowledge of the flow of contrast dye through affected and unaffected tissues in the cerebral arteries.

FIG. 1 shows representative curves of the flow of dye at one location (i.e., a zone of interest) through unaffected (i.e., contralateral vessels; shown as the artery input function) and affected (i.e., ipsilateral vessels; shown as the tissue density curve). As can be seen, contrast dye will generally flow through affected and unaffected tissues differently showing variations as different times to peak dye as well as different slopes for the rise and fall of dye.

It is understood that for a CTP study, up to 50 sequences images would be taken such that the contrast dye curves as shown in FIG. 1 would have a typical resolution as shown by the curves whereas for an mCTA study, images would only be taken at time points $t_0, t_1$-$t_3$ thus having substantially lower resolution of contrast dye flow as compared to the CTP curves.

Figure 1A:
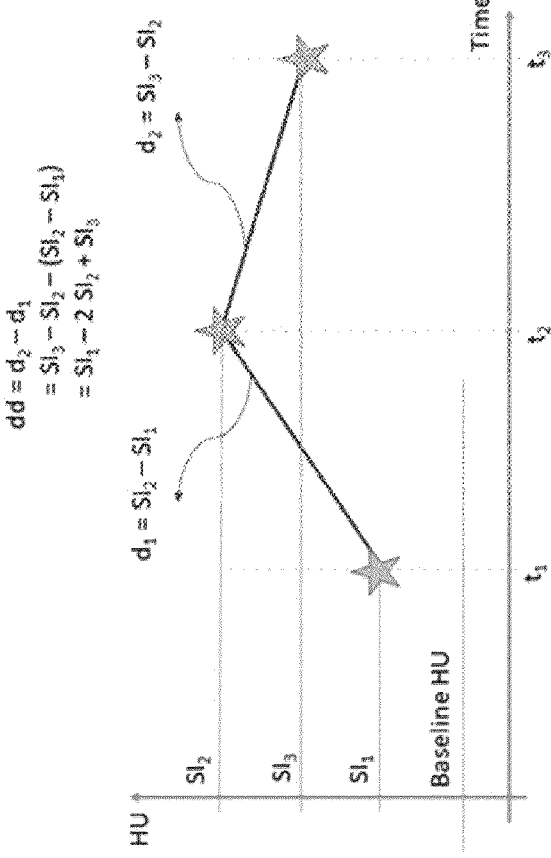
FIG. 1A is a graph showing 3 typical mCTA data points vs. time in accordance with one embodiment of the invention.

For example, as shown in FIG. 1A, only three data points, S1, S2 and S3 representing contrast density at different times are obtained.

Returning to FIG. 1 and with reference to FIG. 2, the difference in flow is explained as follows. As the dye enters the cerebral vessels, the flow bifurcates to the ipsilateral and contralateral vessels. For both CTP and mCTA studies, a series of x-ray images are taken as the bolus of dye enters these vessels. As the contrast flows steadily through the cerebral arteries, the x-ray images will show the relative concentration of dye throughout the arteries at a given time and location on both sides. The relative flow rate of the dye will determine how long the dye will be seen. That is, fast flowing dye will rise in concentration rapidly but also decrease in concentration rapidly (as per the artery input function), whereas slower moving dye will take longer to accumulate and longer to clear (as per the tissue density curve).

Thus, images obtained at different times will show directly and indirectly, the flow of contrast through the brain arteries at the different times. In unaffected vessels, contrast will appear and will have substantially disappeared between to and $t_3$. Further, contrast will peak around $t_1$; be dropping away by $t_2$ and be less than about 25% of the peak of $t_1$ by $t_3$.

For stroke affected tissues, shown as the tissue density curve, the flow of contrast will be time-delayed where for a given location, if contrast is being held up, the peak flow will be time-shifted to a later time, the peak contrast may be lower as compared to unaffected tissues and the time to clear and rate of clearance may be different.

Figure 2:
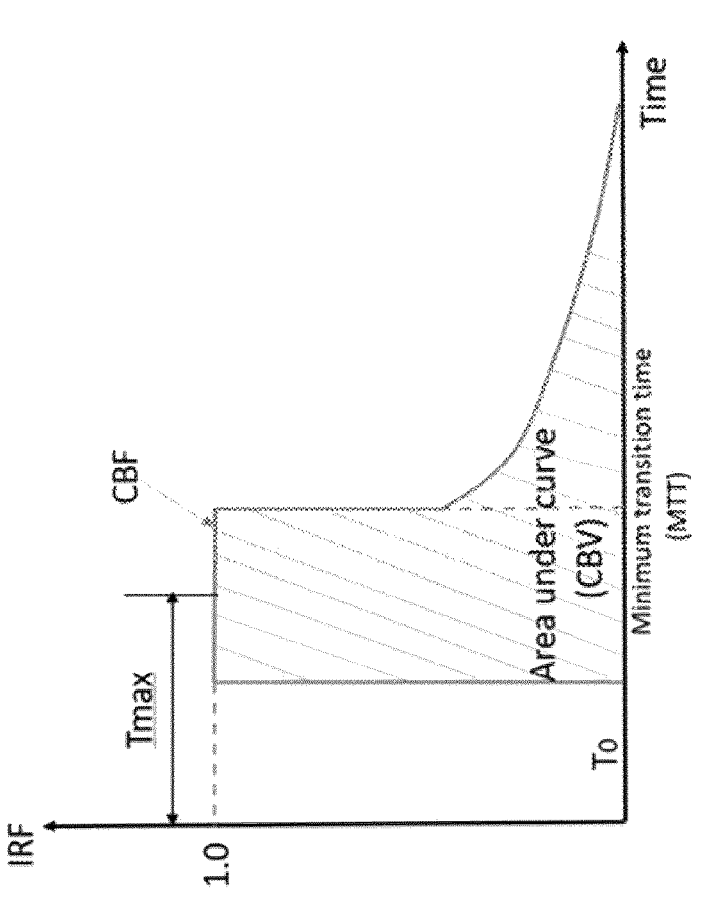
FIG. 2 is a representative graph showing a typical impulse residue function calculated from a deconvolution algorithm in CTP software in accordance with the prior art.

As shown in FIG. 2, after the data has been obtained, for a CTP study the data is processed by deconvolution algorithms to create impulse residual functions and enable various parameters to be assessed.

FIG. 2 shows a number of the physiological parameters that can be derived from the contrast density curves and the impulse residual functions. As introduced above, these include:

a. Mean Transit Time (MTT) which represents the length of time in seconds that it takes for blood to move from arteries to capillaries to veins. MTT=CBV/CBF. An increase in MTT indicates a vasodilatory response to reduced blood flow.

b. Time to Maximum (Tmax) which represents the time at which the maximum value of the residual function occurred and represents a delayed arrival of contrast agent c. Cerebral Blood Volume (CBV) is the area under the FIG. 2 curve and is the volume flow rate through cerebral vasculature per unit time (ml/100 g of brain tissue)

d. Cerebral Blood Flow (CBF) is the maximum value of the FIG. 2 curve and is the amount of blood flowing through capillaries per unit time per unit tissue (ml/min/100 g of brain tissue). It can be used to identify areas of hypoperfusion. Infarct core show decreased CBF by <30%.

Other parameters can be derived including:

e. Time to Peak (TPP) which represents the time in seconds to reach peak voxel enhancement. TPP is an indicator of delayed flow in the setting of stenosis or occlusion and is increased when abnormal.

f. Mismatch Volume is the difference in volume between total hypoperfused area and core infarct and equals penumbra. Mismatch ratio is the ratio of total hypoperfused area and core infarct.

Tmax and CBF are the main parameters used to determine core and penumbra.

From FIGS. 1 and 1A, for a mCTA study, contrast density values are obtained from images taken at $t_1$, $t_2$ and $t_3$. Hence for a given location, as shown in FIG. 1, data points a, b and c are obtained for the ipsilateral side and data points d, e and f are obtained from the contralateral side. Importantly, as minimal data is obtained (as compared to CTP), the peak contrast density between t1 and t2 has not been measured and thus the peak level is not known from a direct measurement.

Machine Learning Models—Development and Testing Overview

Testing and evaluation protocols were developed using three machine learning models including, a core, penumbra and perfusion model, explained in detail below.

The core model seeks to predict the volume of core, the penumbra model seeks to predict the volume of penumbra and the perfusion model seeks to predict tissue perfusion status.

Figure 3:
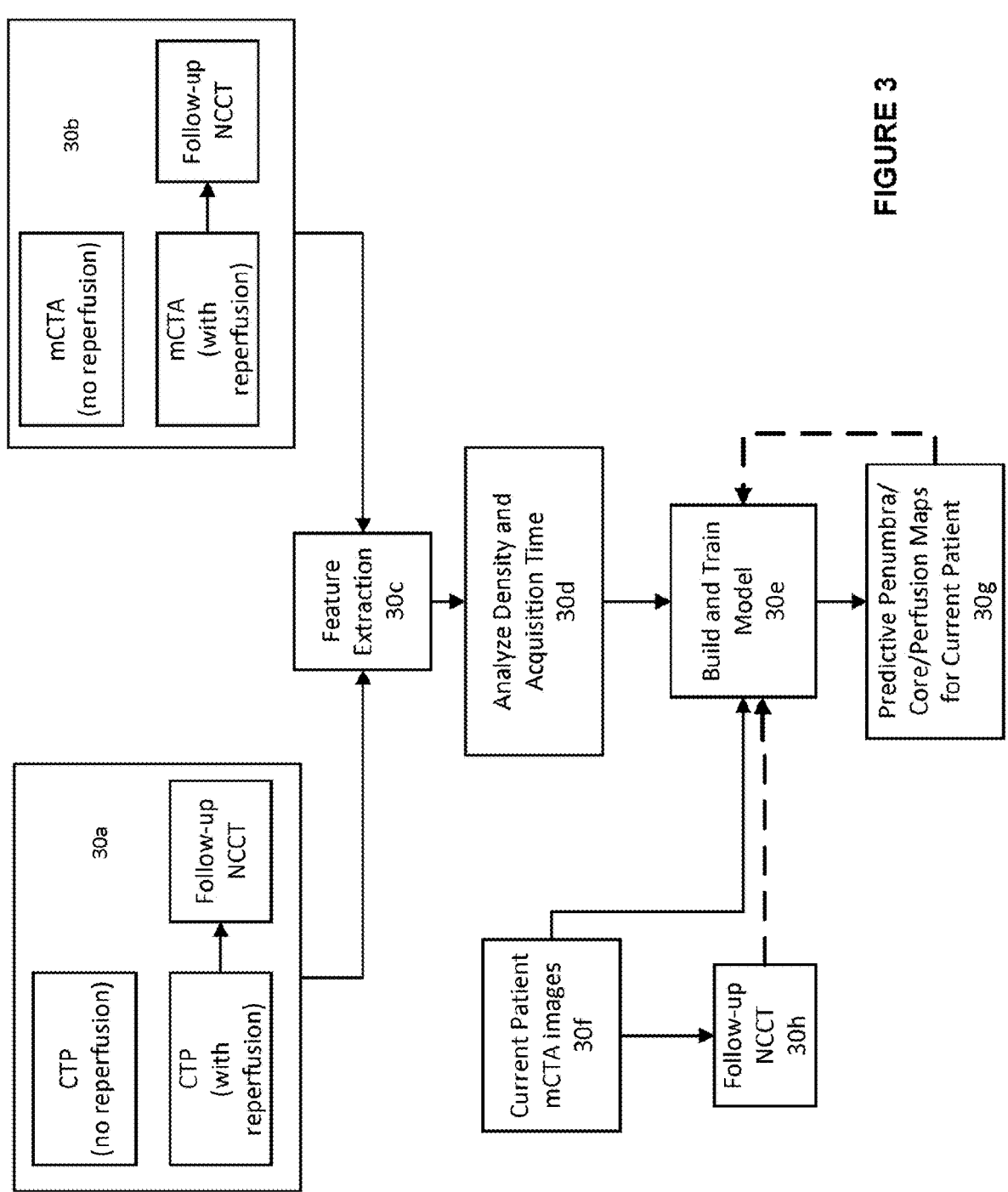
FIG. 3 is a flowchart showing an overall training and testing strategy of a machine learning model to predict ischemic infarct, penumbra and perfusion status in accordance with one embodiment of the invention.

FIG. 3 is an overview of the process for model development, testing, use and refinement. Images from past patients having undergone CTP, reperfusion and follow-up studies 30a as well as images from patients having undergone CTP, no reperfusion and follow-up studies 30b are each subjected to feature extraction analysis 30c and density/acquisition time analysis 30d. Data from these analyses is used to build and train the models 30e. Data from a current patient having undergone an mCTA study 30f can then be introduced into the model 30e to output predictive penumbra/core/perfusion maps 30g for clinical use. Follow up studies on the current patient (eg. NCCT) 30h can be subsequently introduced to the model to enable model refinement.

Figure 3A:
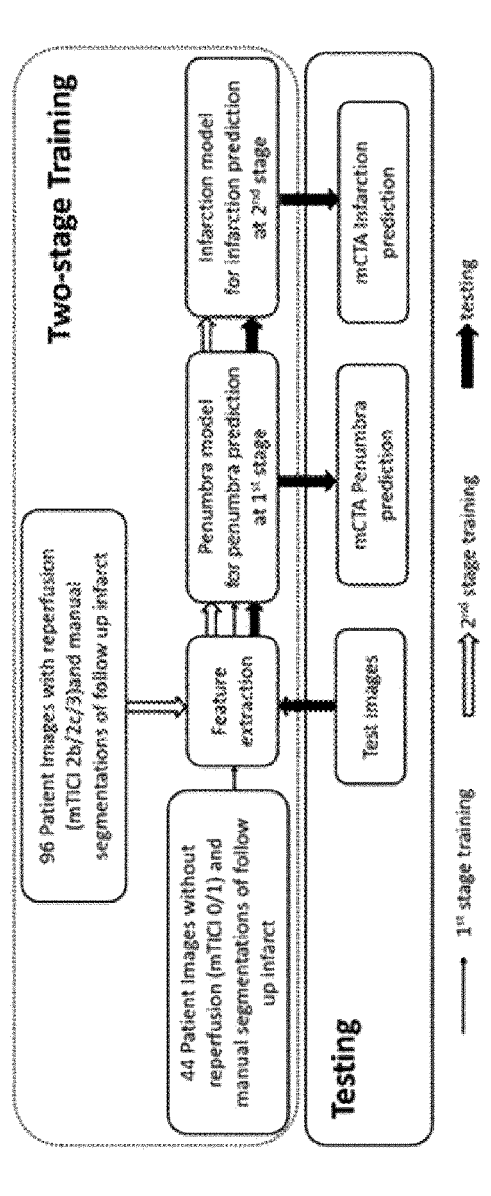
FIG. 3A is a flowchart showing a training and testing strategy of machine learning models to predict (a) ischemic infarct, penumbra and (b) perfusion status in accordance with one embodiment of the invention.
Figure 3A:
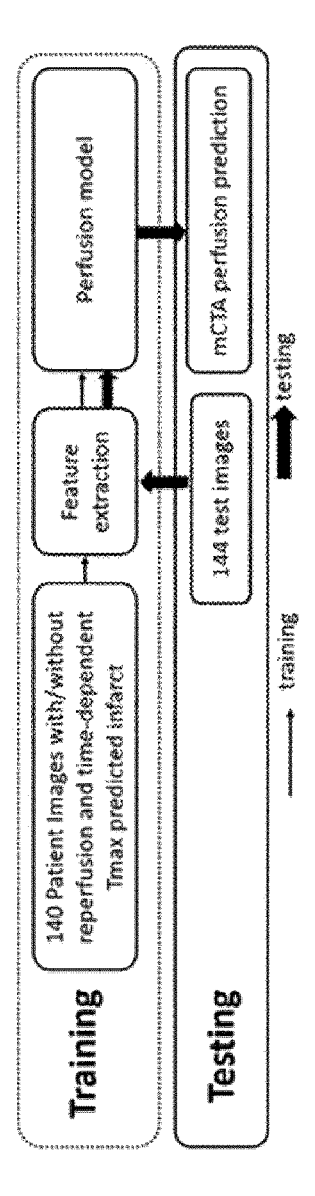

FIG. 3A shows details/example of the process for more specific development/derivation of each of the (a) penumbra, core/infarction prediction maps and (b) perfusion prediction maps. As shown in FIG. 3A(a), images from 96 patients having undergone CTP, reperfusion, and follow-up as well as images from 44 patients having undergone CTP, no reperfusion and follow-up were analyzed for feature extraction. Test mCTA images (including follow up images) were subjected to the same process. After training with all images, using the penumbra model, the model was then tested on the mCTA images (without the follow up images) to predict penumbra for the mCTA images. A similar strategy was then used for infarction/core prediction.

Feature extraction involves analyzing density and acquisition time of areas of interest, namely those areas that may be showing abnormal flow of contrast (ipsilateral side) and the corresponding features on the contralateral side where flow is normal. That is, the steps of feature extraction will examine a baseline density level and look for changes in density across each image. Those areas where density is showing change above a threshold level is marked for further analysis whereas those areas where density does not change above the threshold level will not be marked and not subject to further analysis.

More specifically, zones of interest may be determined by evaluating the following:

1) average and standard deviation of Hounsfield units (HUs) across 3-phase CTA images;

2) coefficient of variance of HUs in 3-phase CTA images;

3) changing slopes of HUs between any two phases;

4) peak of HUs in 3-phase CTA images;

5) time of peak HU.

The size of the zone of interest may be variable and/or adjusted depending on the desired resolution. For example, features were calculated in zones centered at each voxel at three scales (3×3×3, 7×7×7, and 11×11×11 voxels) and then normalized using z-score method.

Analysis of changing slopes between images at different times provides useful information about how quickly contrast agent may be flowing into or out of affected tissues at the scale of individual or a defined number of voxels obtained from the mCTA imaging information. As shown in FIG. 1A, for three phases, three signal intensity (SI) values can be determined (eg. $SI_1$-$SI_3$) relative to a baseline HU (density) value. From these data points, the difference d in SI values between points, enables calculation of the slope of signal intensity change between phases. Slopes may be positive + or negative −. For example, $d_1$, $d_2$ and dd are defined as follows:

$$d_1 = Sl_2 - Sl_1$$

$$d_2 = Sl_3 - Sl_2$$

$$dd = d_2 - d_1$$

$$= Sl_3 - Sl_2 - (Sl_2 - Sl_1)$$

$$= Sl_1 - 2Sl_2 + Sl_3$$

dd is the $2^{nd}$ derivative of the change of slope between two lines. The slopes of each of $d_1$, $d_2$ and dd are calculated together with their sign (i.e., + or −) and used as a basis for understanding the contrast delay for a particular location which can then be used to assign a tissue health value to that location.

Figure 4:
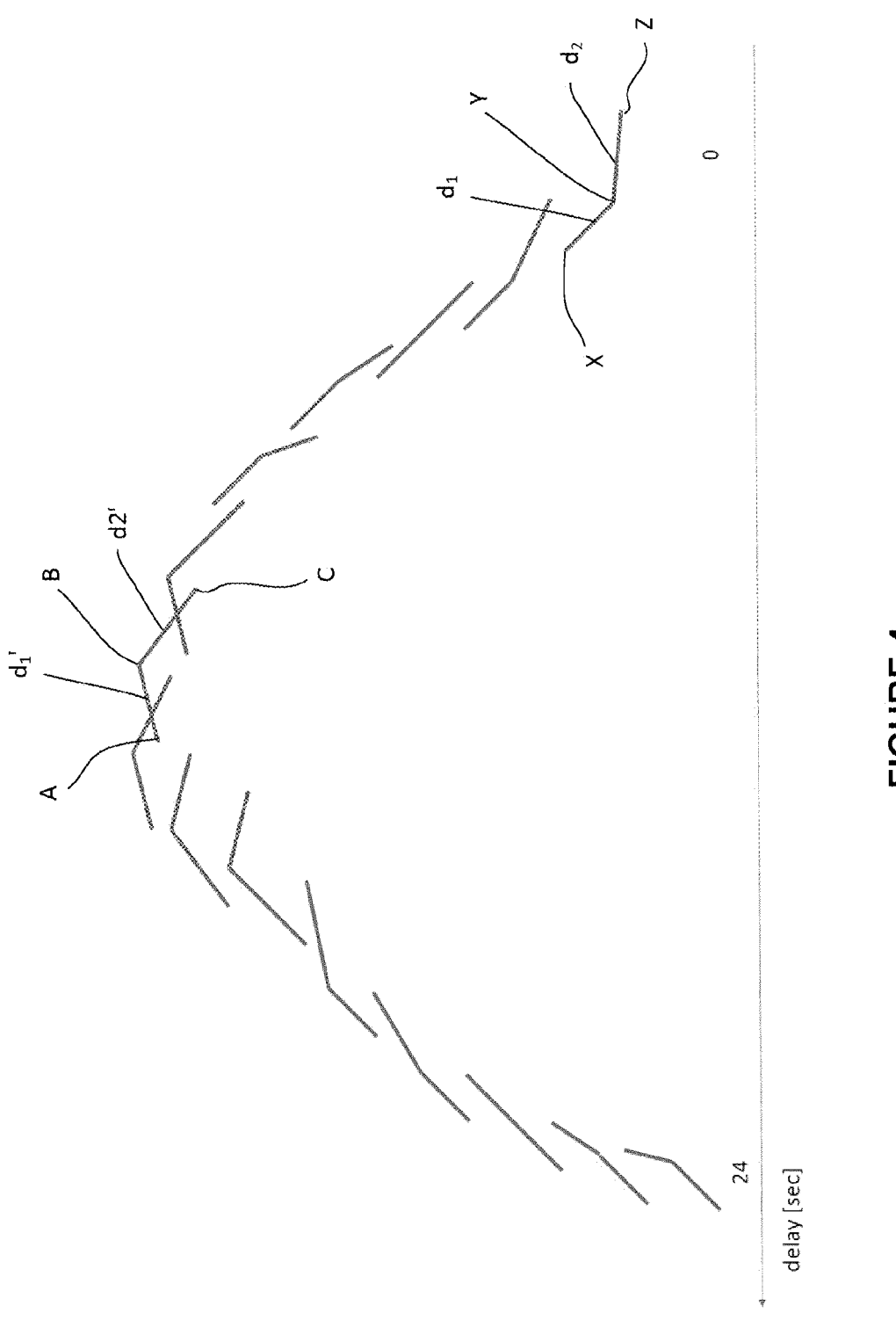
FIG. 4 is an illustration showing $d_1$, $d_2$ and dd patterns in accordance with one embodiment the invention showing representative contrast delay for different patterns.

FIG. 4 is a representation of how the slopes may vary based on the relative delay of contrast arriving at a particular location. For example, if there is substantially no delay of contrast arriving at the ipsilateral location of interest, one would expect flow characteristics of normal tissue. Three-point line pattern 40, shows points X, Y and Z defining two lines having slopes $d_1$, $d_2$. As shown in FIGS. 1, X, Y and Z are similar to points d, e and f on the artery input function. Similarly, three-point line pattern 42, shows points A, B and C defining two lines having slopes $d_1'$, $d_2'$ which are similar to points a, b and c on the tissue density curve of FIG. 1 and shows the delay. As contrast is increasingly held up, the tissue density curve as shown in FIG. 1 will be time-shifted to the right; thus, producing three-point line patterns similar to those shown in FIG. 4.

Accordingly, depending on the time delay, each three-point line pattern will have a range of profiles as shown in FIG. 4 where the time delay increases from the right to left direction.

Figure 4A:
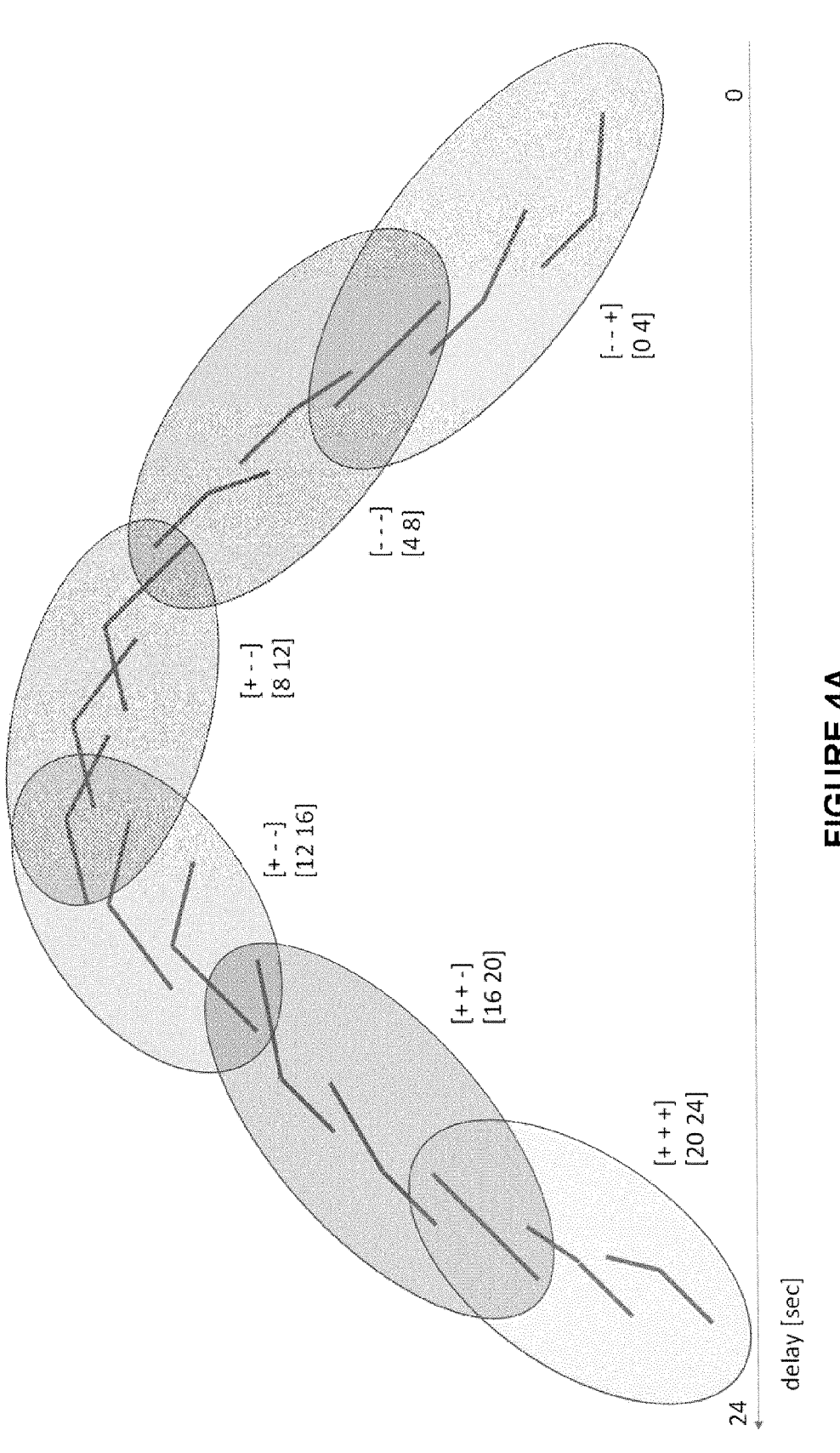
FIG. 4A is an illustration showing $d_1$, $d_2$ and dd patterns as in FIG. 4 overlaid with representatives zones for color coding in accordance with one embodiment of the invention.

The ±patterns of the calculated $d_1$, $d_2$, dd values represent different scenarios of contrast flow as shown in Table 2 and FIG. 4A which shows the different patterns together with representative circulation value ranging from 1 (good flow) to 5 (poor flow) which can be indicative of relative tissue health. Information about how contrast is flowing to a location and out of a location can be determined from each three-point line function.

TABLE 2

| d-Slope Interpretation and Representative Tissue Health Coding on Ipsilateral Side | | | | | |
|---|---|---|---|---|---|
| Group Patterns | $d_1$ | $d_2$ | dd | Interpretation | Relative Circulation Value |
| 44a | − | − | + | Voxel showing shortest delay (if any) of contrast reaching the location. | 1 |
| 44b | − | − | − | Voxel showing next shortest delay in contrast reaching the location. Contrast has reached the voxel quickly and is showing a slight delay in contrast washout | 2 |
| 44c, d | + | − | − | Voxel showing peak contrast density at around the time the phase 2 image was taken. | 3 |
| 44e | + | + | − | Voxel showing that contrast density is starting to peak at around the time the phase 2 image was taken. | 4 |
| 44f | + | + | + | Voxel showing greatest delay. Across all phases, contrast density is continuing to rise. | 5 |

** combinations of [− + −] and [+ − +] are not mathematically plausible.

Each group pattern can be provided with threshold values to determine which group a particular line pattern may be categorized within. Different groups may be defined with individual, or a range of colors used for subsequent color mapping of a particular voxel. The above analysis is performed for each voxel of an image volume of interest.

To obtain meaningful prediction data, group patterns are matched to past data showing similar patterns.

Figure 4B:
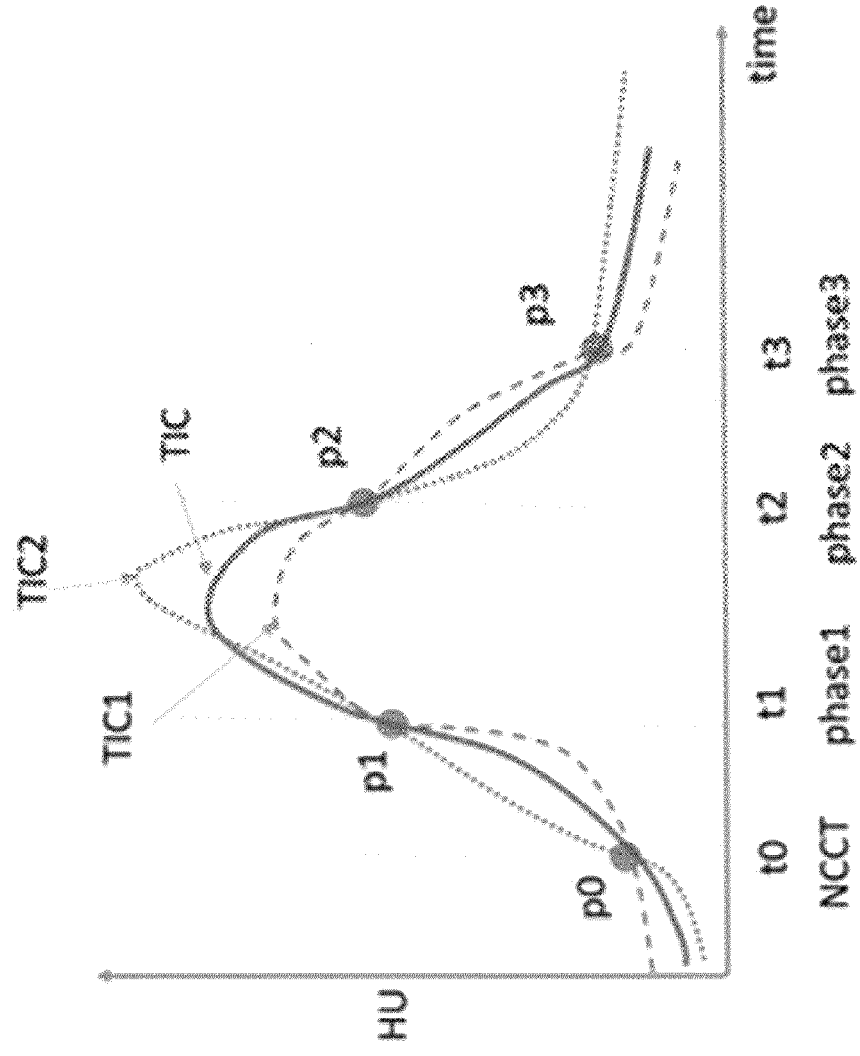
FIG. 4B is a representative graph of data points from a set of mCTA images having p0-p3 data points and showing how tissue intensity curves (TICs) from past studies have been matched to the data points.

As shown in FIG. 4B, the group pattern determined above can be matched to past patient images showing similar group patterns. For example, FIG. 4B shows 3 tissue input curves, TIC, TIC1 and TIC2 which represent the data from 3 CTP studies and with "matching" phase data points p1-p3 and baseline p0. As each of the CTP studies have determined penumbra, core and perfusion maps, data from past studies provides a range of values for penumbra, core and perfusion which can thus be used to provide a basis for predicting these values for the current patient and used to generate 2- and/or 3-dimensional color-coded image/maps. That is, data from the past studies can be processed by appropriate deconvolution algorithms to generate CT perfusion maps such as Tmax, CBV and CBF for each TIC from the past studies.

Model Development-Machine Learning

Referring back to FIGS. 3 and 3A, as noted above, mCTA images as well as NCCT at baseline are introduced into the model and matched to the best fit within the CTP datasets to provide both an mCTA penumbra prediction and mCTA core prediction.

Hence, a prediction of Tmax, CBV and CBF for each can be estimated for the 3-phase mCTA study based on the CT perfusion maps from the past studies.

Figure 4C:
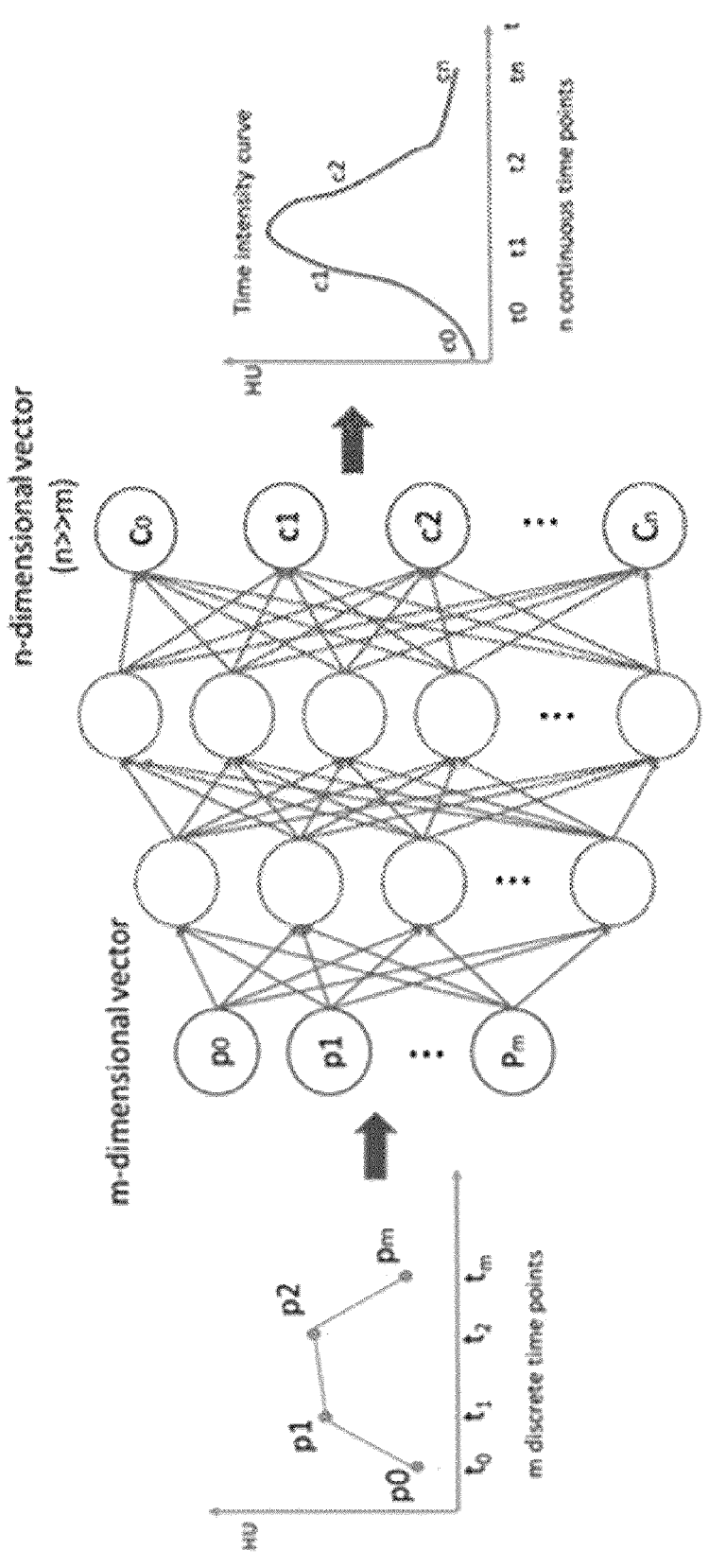
FIG. 4C is a figure illustrating a process of machine learning in accordance with one embodiment of the invention.

In one embodiment, as shown in FIG. 4C, machine learning techniques such as deep neural network can be used to interpolate a TIC having p0-pm points at discrete time points to create a predicted TIC represented by continuous data points CO-Cn, which can then be utilized to build predicted CT perfusion maps.

Figure 5:
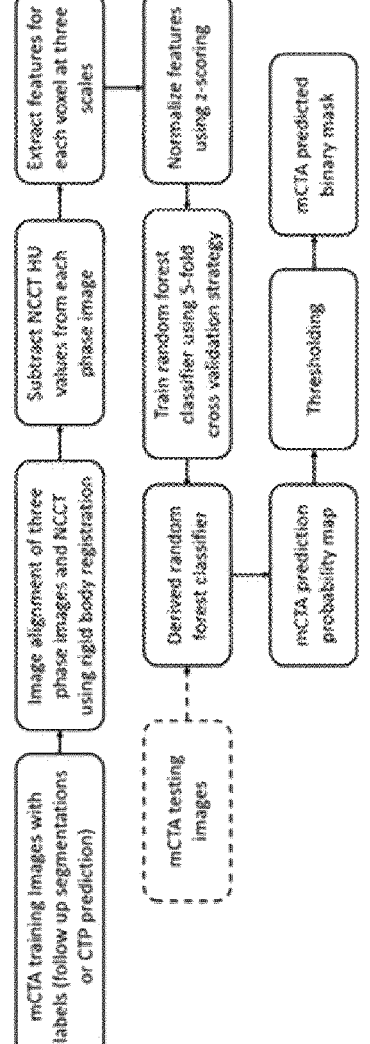
FIG. 5 is a flowchart showing details of training and testing each of three machine learning models.

In further detail, as shown in FIG. 5, in one embodiment, the following steps were undertaken in processing the mCTA images to build the models.

Step 1-Analysis of data from mCTA images a. Pre-processing mCTA training images. This includes spatially aligning 3-phase mCTA and NCCT at baseline in order to correct patient movement during acquisition; and standardizing density values of mCTA by subtracting density value of NCCT from each phase CTA at each voxel location.

b. Analyzing the mCTA images and identifying features of interest for each voxel location wherein the features of interest are derived from density values across three phases and acquisition time of each phase of the mCTA. These features of interest are extracted and includes data from infarcted and normal tissue on the ipsilateral side as defined by the follow-up imaging. This information was then normalized by comparing it with the ipsilateral hemisphere via a z-scoring method. The z-scoring method was performed by subtracting the mean value of an image and divided by the standard deviation of the image.

Step 2-Training a. Training a random forest classifier using the features of interest from step 1b while using follow up infarct segmentation as an indicator. For example, a "1" is assigned to represent an infarct voxel whereas a "0" is assigned to represent normal tissue. This information is then used to generate a penumbra probability map, indicating how likely a voxel in mCTA will be infarcted if no reperfusion is achieved. Random forest classifier is an ensemble learning method for classification that operates by constructing a multitude of decision trees at training time and outputting the class that is the mode of the classes (classification) of the individual trees.

Step 3-Applying a Threshold a. Applying a threshold on the probability map from step 2 to generate a binary mask of penumbra tissue. For example, a "1 in this binary mask represents an infarct voxel whereas a "0" represents normal tissue.

Other Modelling Techniques

The machine learning model may be constructed using other modelling techniques including support vector machine, neural network and/or k nearest neighbor techniques.

Model Validation

After predicted core, infarction and perfusion maps are created, correlation to the "actual" outcome can be made to determine the accuracy of the models. As discussed below in the validation study, the models were statistically validated.

Additional System and Model Functionality

The models are effective in assisting a physician in making treatment decisions during diagnosis. As discussed above, for patients with acute ischemic stroke, time to treatment is well correlated to patient outcome; hence obtaining effective information to enable a physician to make a treatment decision as soon as possible is desired. As such, the steps to determine and present core, penumbra and perfusion status from the time current mCTA images are introduced into the system are ideally completed in 10 minutes or less.

Additional data can also be introduced into the past patient database and presented as additional information to the physician. In one embodiment, the past patient database includes information about patient outcome following treatment or not as may be input after an NCCT follow-up study has been completed. Thus, upon creating a prediction map as described above for the current patient, data from one or more of the closest match past patient studies describing patient outcome may be presented to the physician. Such outcome data may be a quantified and standard assessment score as known. For example, a past patient study may include treatment information that a successful thrombectomy at a particular region of interest was completed within 40 minutes of images being obtained and the patient made a good recovery. A second past patient study showing similar map information may include information that treatment occurred in 90 minutes and that patient recovery was poor. As such, the physician can use this information as additional information to evaluate if they should initiate a specific treatment.

In other embodiments, likelihood of success of a treatment may be presented and be correlated to any one of or a combination of predicted core, penumbra and/or perfusion status.

In other embodiments, features of interest and patterns relating to occlusion location, core, penumbra and perfusion, include any one of or a combination of the first-order statistics, such as mean and histogram of HU values, and texture features, such as gray-level co-occurrence matrix and gray level run length matrix.

The features of interest relating to occlusion location, core, penumbra and perfusion are calculated at different scales; for a given voxel corresponding to the axial imaging, the features are calculated at low, median, and high-resolution scales.

In various embodiments, the features of interest mostly contributed to occlusion location, core, penumbra and perfusion are automatically or manually selected using feature selection technique in order to improve prediction accuracy, reduce overfitting, and reduce training time. The feature selection technique includes univariate selection, feature importance, and correlation matrix with heatmap.

In various embodiments, each probability map is thresholded to generate infarct core and/or penumbra and/or perfusion volume for the axial imaging slice.

In other embodiments, morphological operations including image dilation and/or erosion and component analysis are applied after thresholding to remove isolated islands.

In another embodiment, the machine learning model enables prediction of a combination of core and penumbra from a multiple label machine learning model, that is, label 1 denotes core, label 2 denotes penumbra, and label 3 denotes normal tissue. The single model can predict core and penumbra at the same time.

Figure 6:
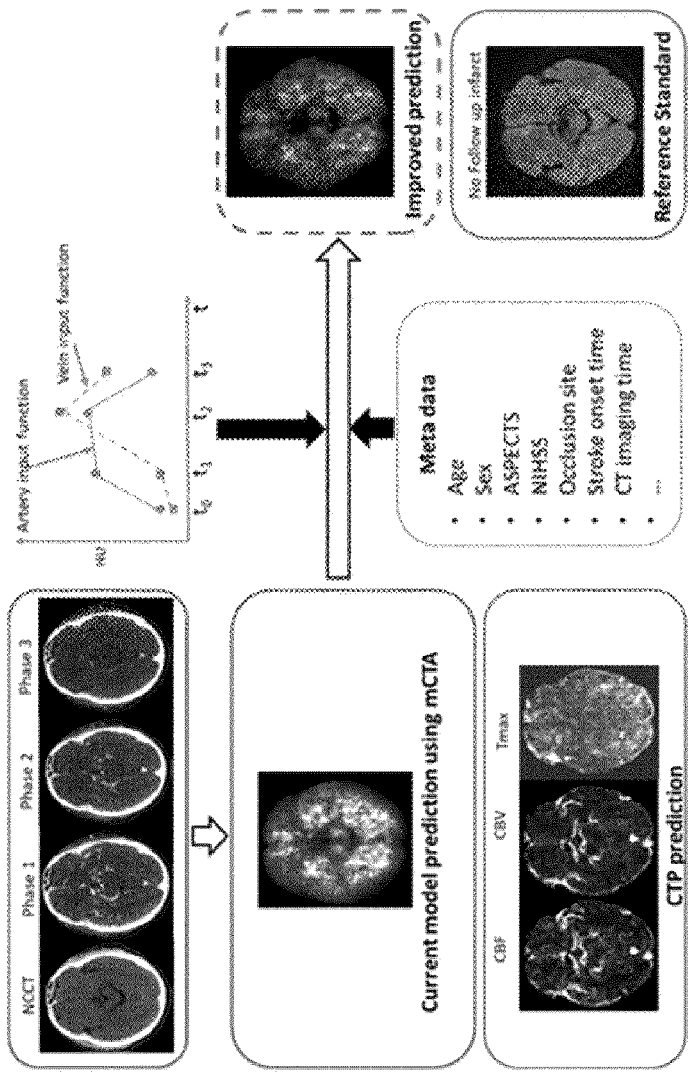
FIG. 6 is an overview of input images and input data including patient meta data and input artery/vein functions together with representative output data that may be displayed after modelling and prediction.

In other embodiments, as shown in FIG. 6 features at a patient level are selectively used as inputs, such as artery and vein input functions manually or automatically selected, together with meta data including age, sex, NIHSS, ASPECTS, occlusion site.

Case Examples

FIG. 6 shows a hypothetical example, in which, artery and vein input functions and meta data are used as additional features to refine the developed machine learning model and better predict tissue status, especially for the patients with small or no occlusions.

Figure 6A:
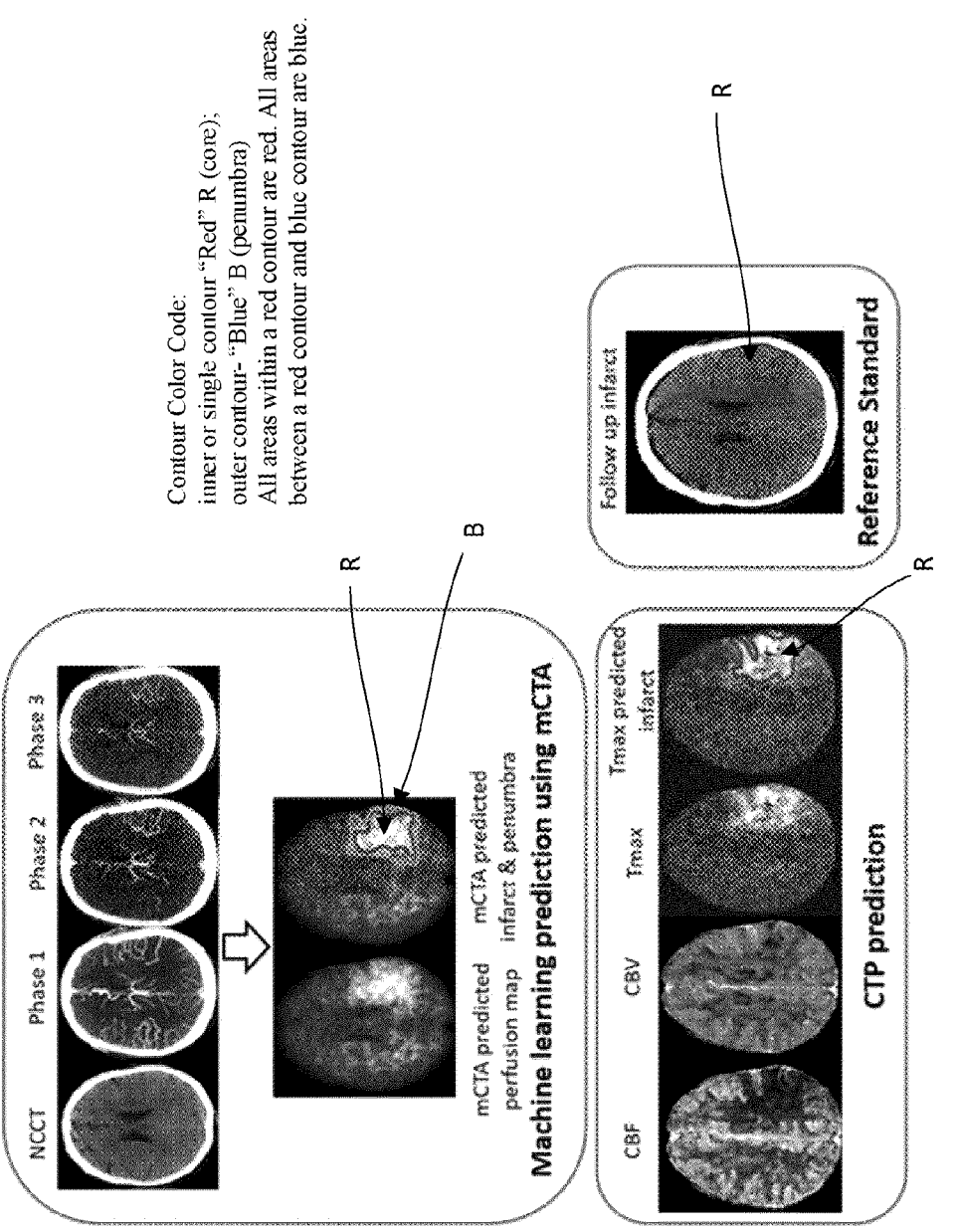
FIGS. 6A and 6B are representative mCTA and prediction maps from two case studies.
Figure 6B:
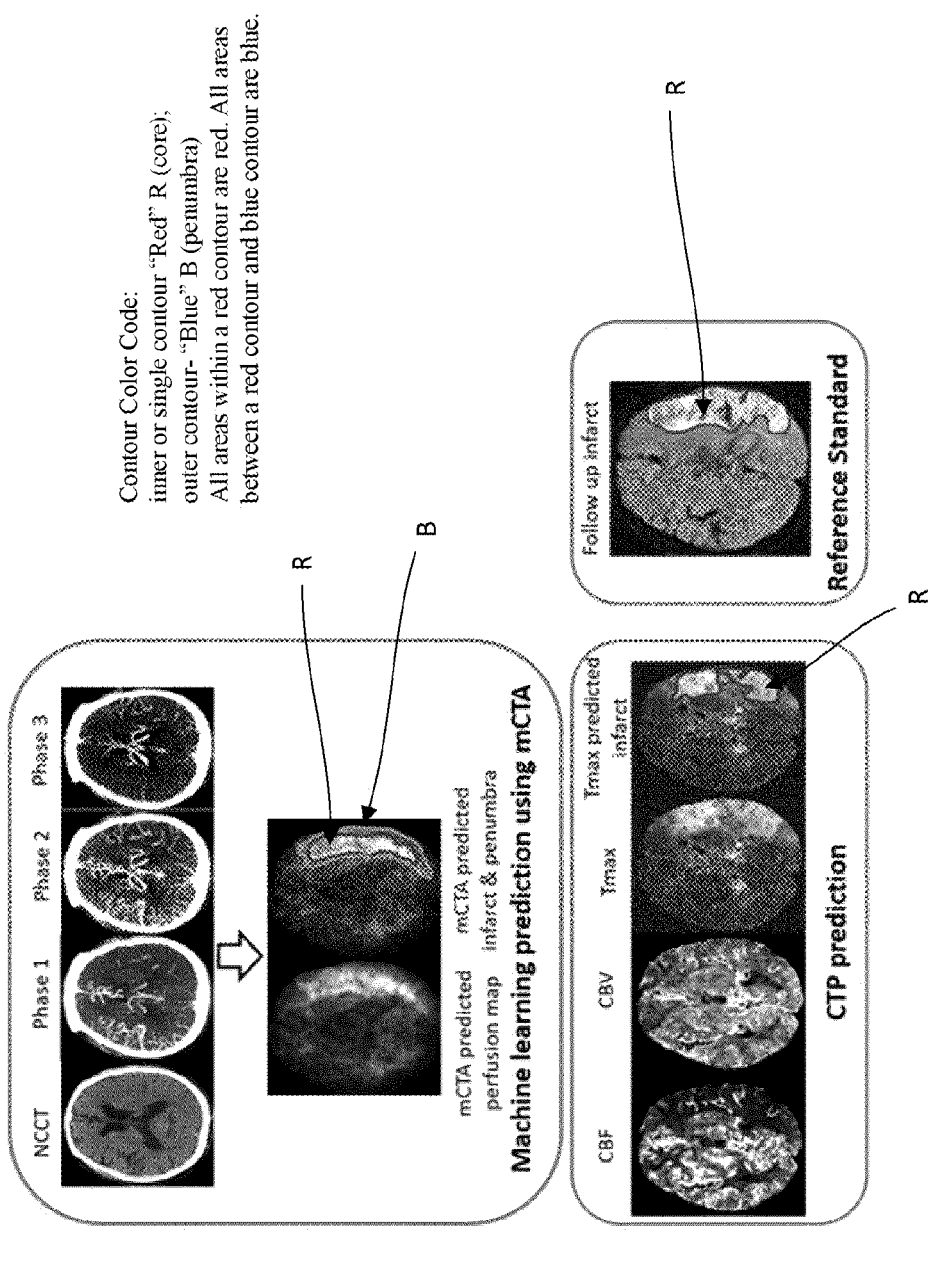

FIGS. 6A and 6B are examples of application of the system to create effective diagnostic maps. FIG. 6A shows representative mCTA images for an 83 year old female showing a left ICA occlusion with a stroke onset to CT time of 95 mins, NIHSS 23, and ASPECTS 10.

FIG. 6B shows representative mCTA images for an 87 years old male showing left distal M1 occlusion with a stroke onset to CT time of 208 mins, NIHSS 28, and ASPECTS 5.

Medium Vessel Occlusion (MeVO) Tool and Use

Figure 7:
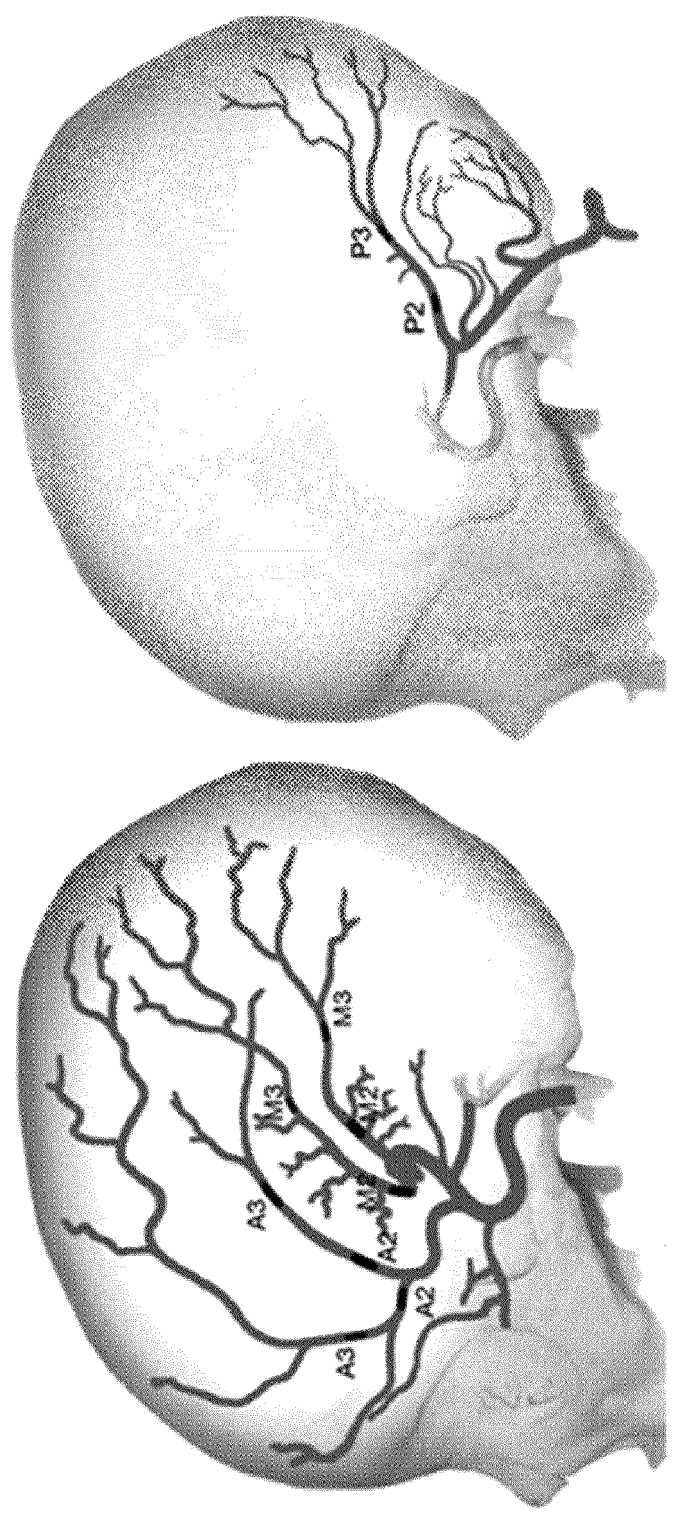
FIG. 7 is a representative image showing anterior, middle, and posterior arteries at levels 2 and 3 in accordance with the prior art.
Figure 7A:
FIGS. 7A-7H are a sequence of images in a patient showing a progression of a diagnostic process using mCTA prediction maps and MeVO prediction tools together with conventional imaging.
Figure 7B:
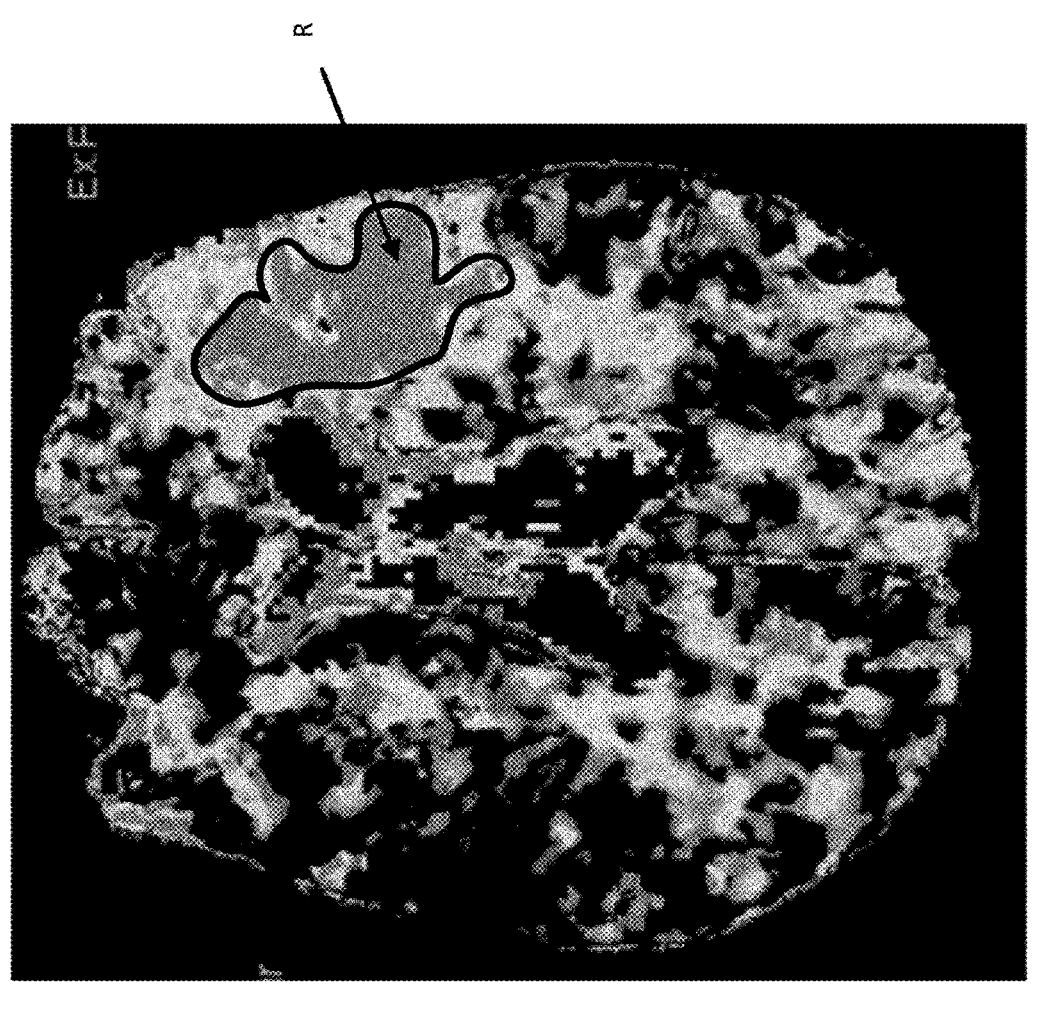
Figure 7C:
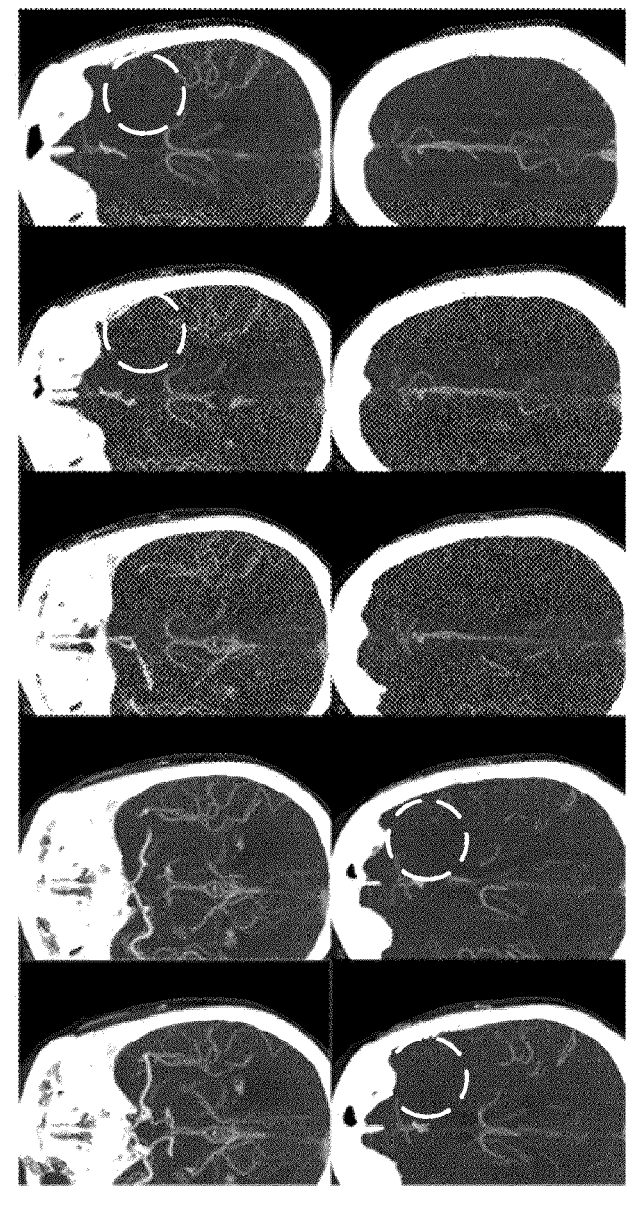
Figure 7D:
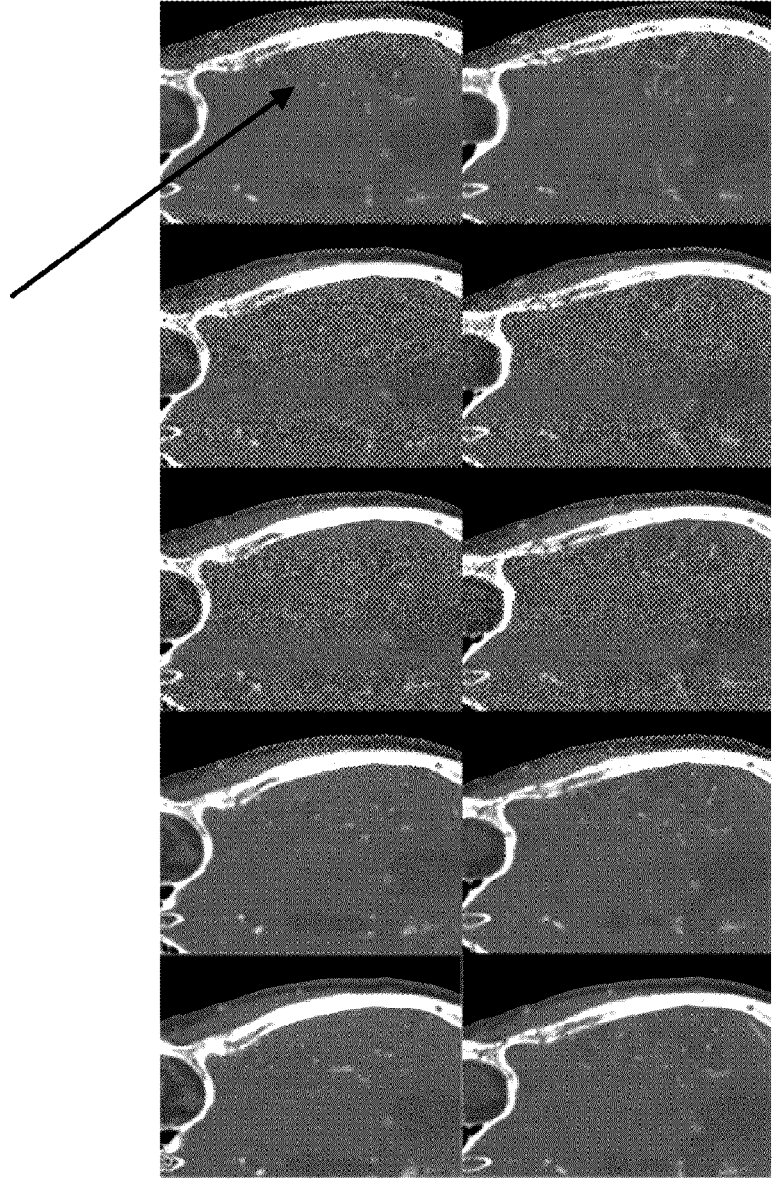
Figure 7E:
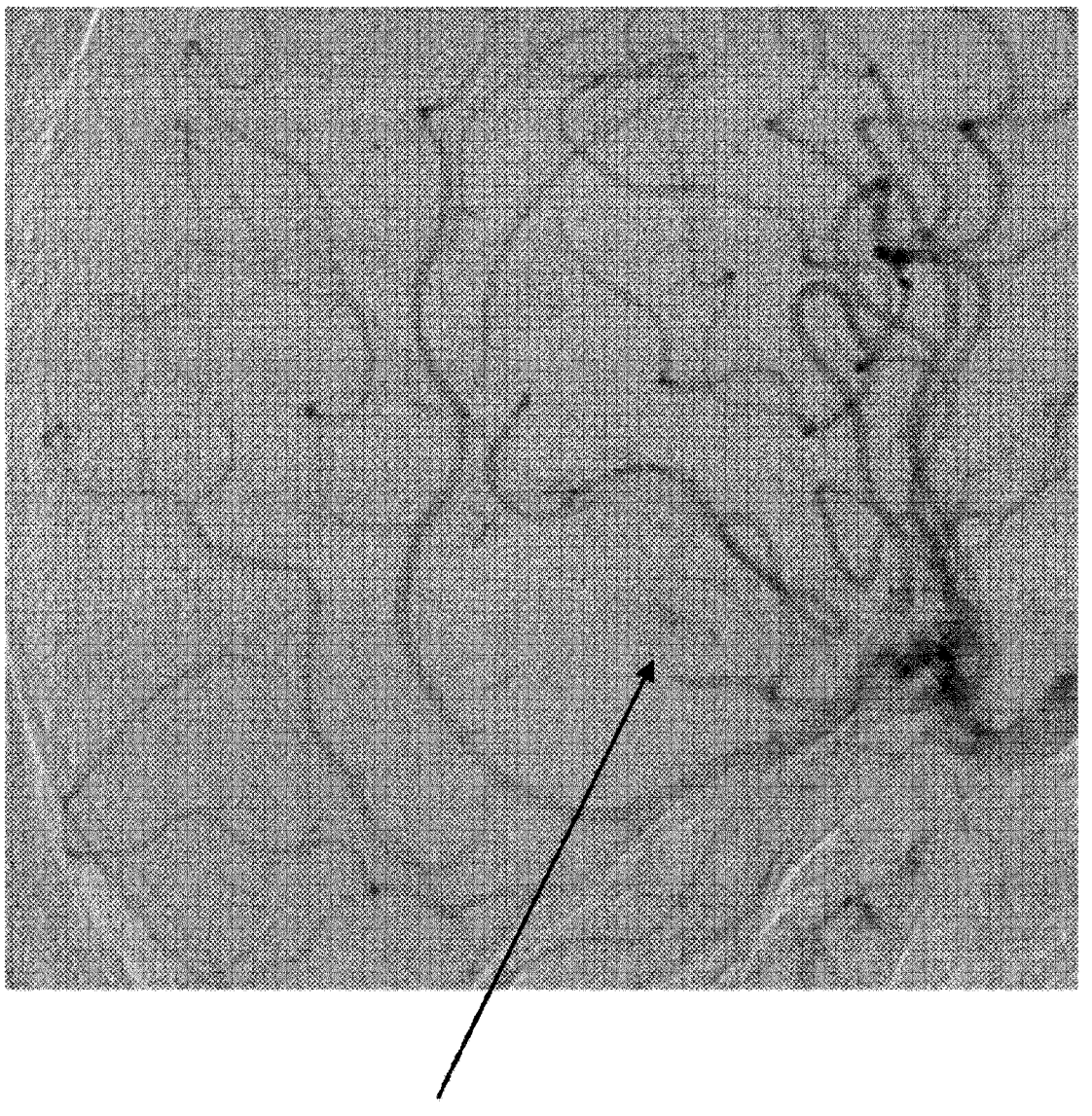
Figure 7F:
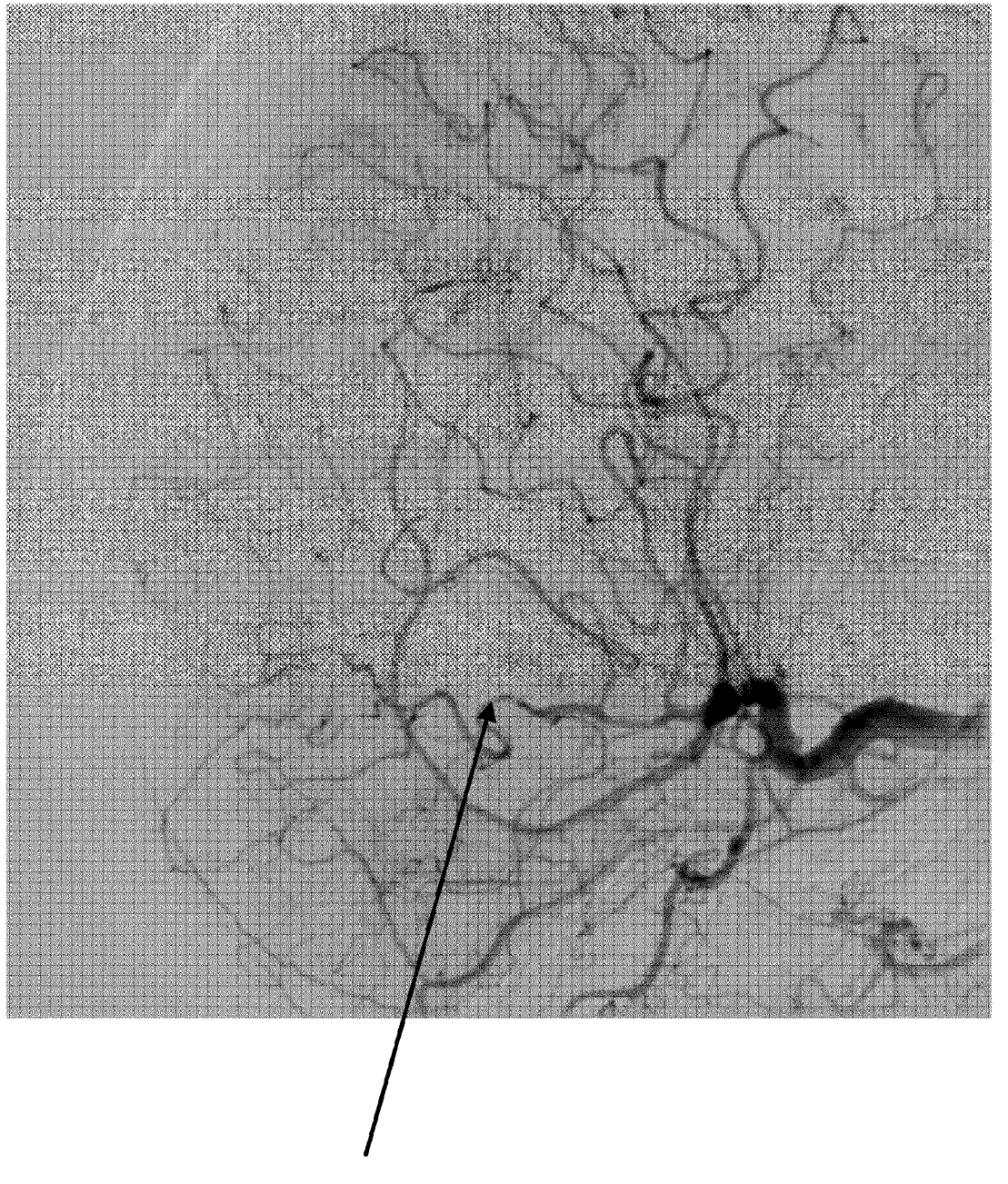
Figure 7G:
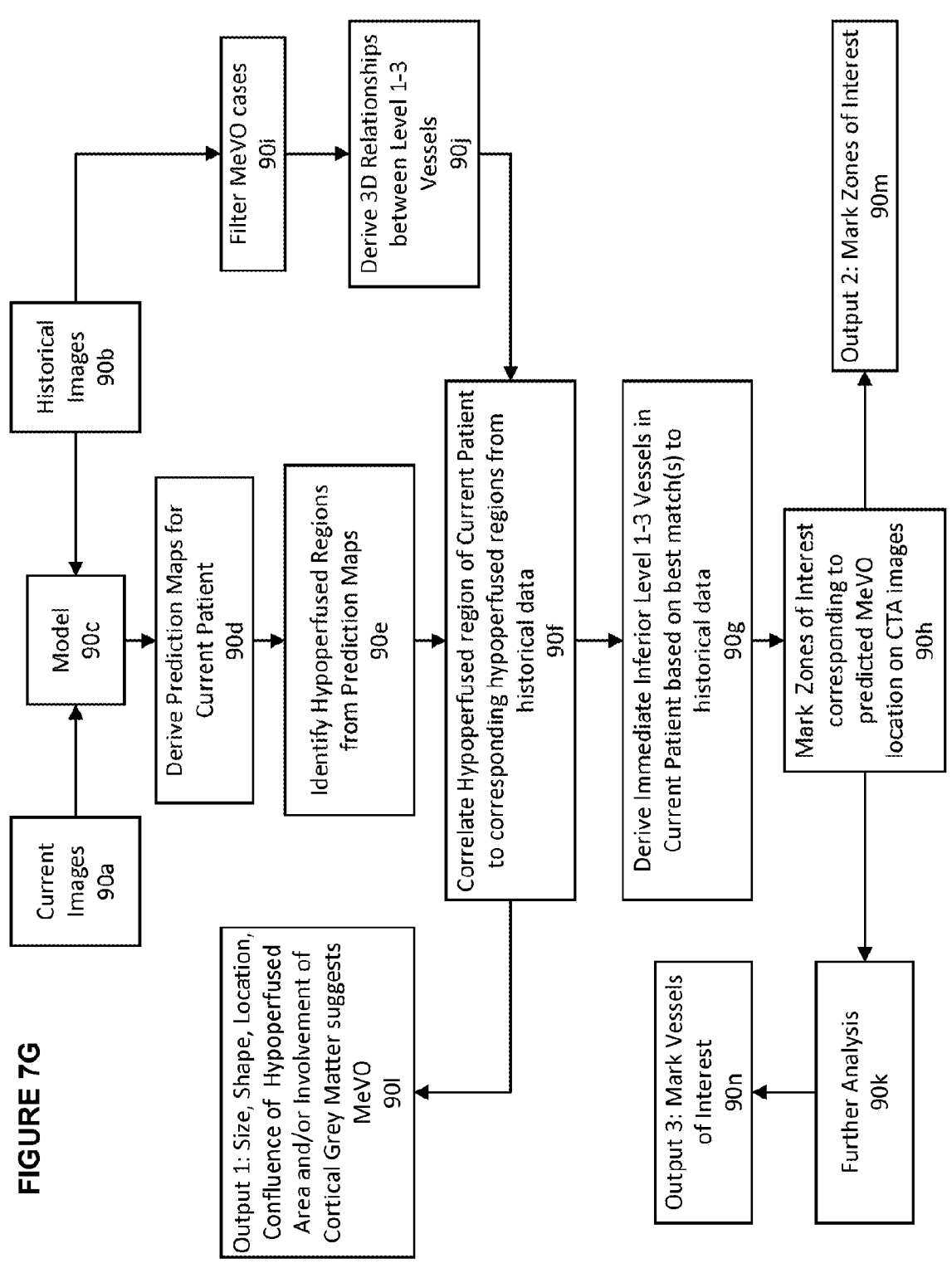
Figure 7H:
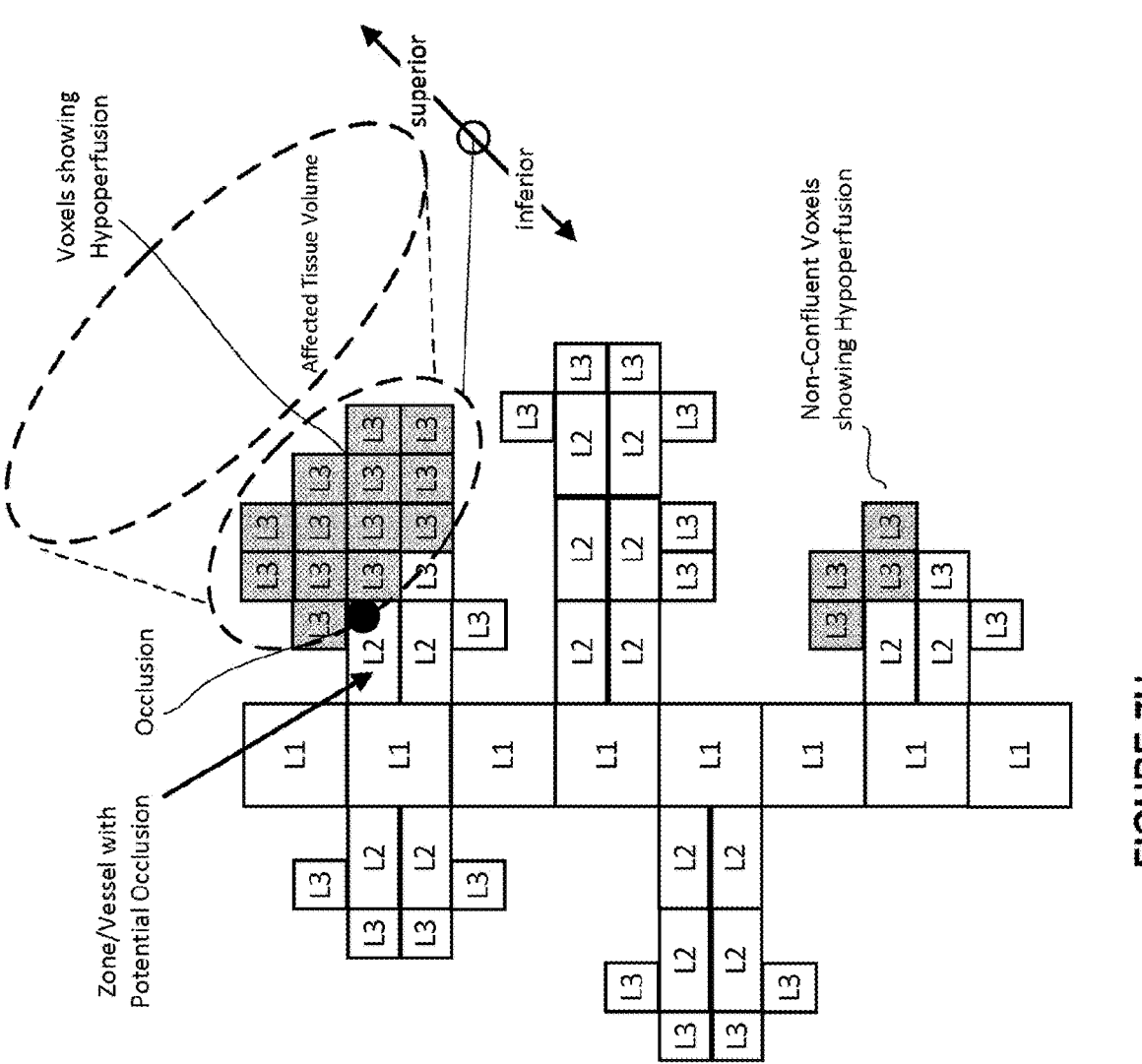

In various embodiments as illustrated in FIGS. 7-7H, the system may additionally be used to assist in diagnosing MeVO and provide different outputs to a diagnosing physician with varying levels of detail that may be relevant to treatment decisions. As described below, levels of output may include:

a) a simple indication that MeVO (as opposed to LVO or SVO) is likely present, b) identification of zones of interest where MeVO may be present; and/or, c) specific identification of locations/vessels where MeVO may be present.

Improved MeVO detection is achieved through utilization of CTA images and/or with prediction maps (e.g., core/penumbra/perfusion) together with additional functionality within the system including anatomical maps built from a plurality of patients and/or knowledge obtained by prediction models/learning algorithms as described above.

For example, in one embodiment, as with the general prediction map system described above, the MeVO system/tool is trained with past images and used to create effective prediction maps for a current patient that can be used to locate and quantify hypoperfused tissue and subsequently evaluate if the parameters of the hypoperfused tissue are indicative of MeVO.

In accordance with one embodiment, the steps of identifying MeVO may be achieved automatically or semi-automatically by the following general process:

a. Assess location of affected tissue from various combinations of CTA images, CTP studies, mCTA studies as may be available.

b. From the hypoperfused area, define a general zone of interest where MeVO may be present.

c. Determine additional parameters of the affected tissue including the shape, size/volume, confluence, involvement of the cortex and sub-cortical white matter and knowledge of the known supply by vessels in that region.

d. Determine the 2D/3D position, size, and shape of the hypoperfused area. The position, size and shape is determined by assembling voxels showing affected tissue characteristics that share a boundary with adjacent voxels showing affected tissue in both proximal and distal positions. The assembled voxels define a quantifiable volume (i.e., based on a calculated number of linked voxels) and shape characteristics (e.g., a characteristic "cone", "frusto-conical" or "wedge" shape in the distal direction). The location of the volume is compared to known regions of the brain based on general knowledge of brain anatomy or specific knowledge of brain anatomy from a match/correlation analysis (as described below). Table 3 shows various characteristics that can be assessed.

e. Determine if the hypoperfused volume is LVO, MeVO or SVO based on the analysis in step d.

TABLE 3

| Characteristic | LVO | MeVO | SVO |
|---|---|---|---|
| Volume (ml) | Range: 80-400 Common: 150-180 | Range: 25-80 Common: 30-70 | <25 |
| Shape | Cone/Wedge | Cone/Wedge | Often indeterminate |
| Confluence | Yes | Yes | No |
| Cortex | Involved | Mostly | Maybe |

TABLE 3-continued

| Characteristic | LVO | MeVO | SVO |
|---|---|---|---|
| Sub-cortical white matter | Involved | Involved | Maybe |
| Possible sites of Occlusion per hemisphere | 1-2 | 6-20 | >20 (often beyond resolution of CTA) | f. If it is determined that MeVO is likely, additional analysis can be conducted depending on the desired outputs as described above. If greater precision is desired a zone of interest analysis can be conducted to highlight a zone(s) on the images where further investigation could be conducted. A vessel of interest analysis may also be conducted to identify a vessel(s) of interest. Generally, to conduct these analyses:

i. Contrast densities from adjacent proximal voxels from one or more phases of CTA images are searched for variations in contrast density that may signal that contrast is flowing normally or abnormally within one or more nearby voxels.

ii. Voxels that indicate normal contrast flow may be discarded from further analysis and/or be utilized as a baseline for determining if contrast is abnormal or normal in nearby voxels.

iii. Voxels indicating abnormal contrast flow may be flagged for further analysis.

iv. For those voxels showing abnormal flow, additional analysis is conducted to highlight zones/vessels where contrast abruptly transitions from no contrast to significant contrast between adjacent images or vice versa.

v. Highlighted zones and/or vessels may be automatically marked on CTA images as a suggestion to the physician to focus attention in a particular area.

The foregoing is illustrated by the following illustrative example. As noted above, FIG. 7 is a representative figure showing the structure and distribution of level 1-3 vessels. From known anatomy, a general pattern of interconnected volumes can be built through successive levels from proximal to distal vessels as shown schematically in FIG. 7H. That is, L1 vessels as represented by individual voxels may be positioned in 2D/3D space. L2 vessels are represented by voxels surrounding or branching off the L1 vessels to a defined distance and L3 vessels are represented by voxels surrounding the L2 vessels to a defined distance.

Thus, from a prediction map, a hypoperfused zone may be identified and correlated to a 3D location (for example, a particular M2/M3 zone) and thus to a general location in the brain. With knowledge that vessels proximal to that location are generally perfused by adjacent areas in a known direction, corresponding proximal voxels on the images may be flagged for additional investigation.

Importantly, voxels that may be distal and/or beyond a particular threshold distance from the hypoperfused area may be discarded from further processing. Similarly, proximal voxels beyond a threshold distance may also be discarded.

Further processing can look for a variety of changes within those flagged voxels, including normal and abnormal contrast flow and/or collateral filling from a later CTA image.

In one embodiment, different phases of voxels (e.g., from mCTA) are overlaid with respect to one another to help identify a "missing vessel" i.e., one where no contrast is directly observed but contrast behaviour nearby suggests its presence.

FIG. 7G describes a process of providing additional information to a physician in accordance with one embodiment to assist in diagnosing MeVO. In this example, output to the physician is derived from a combination of current patient images 90a and historical images 90b which are utilized by a model 90c as generally described above. From the model, prediction maps (eg. core/penumbra/perfusion) 90d are analysed to identify hypoperfused regions 90e in a current patient typically marked by color coding. Analysis to determine if the hypoperfused volume is likely LVO, MeVO or SVO is conducted. If MeVO is suggested 90e, these maps are correlated to specific 2D areas/volumes in the brain of the current patient and can then be compared and correlated to corresponding hypoperfused areas from historical data images 90f. The best fit historical data images, having associated L1-L3 mapping data, is/are used to identify corresponding proximal zones in the current patient images 90g, which are marked as zones of interest for the physician to examine for further MeVO diagnosis.

In various embodiments, historical images may be filtered to limit the dataset to MeVO images only 90i.

In addition, and prior to comparison with current patient images, 2D/3D relationships between level 1-3 vessels can be derived 90j and as shown in FIG. 7H, wherein numerous volumes of tissue are assembled into a successive branch structure in 2D/3D space. FIG. 7H shows a graphical representation of voxels labelled according to their level and that based on their level may touch voxels of the same label or one level higher/lower. That is, a level 1 voxel can only directly touch/communicate with a level 2 voxel etc. Shown as a representative 2D and partial 3D map, FIG. 7H shows two zones where a number of L3 voxels are grey representing the color code for hypoperfused tissue as shown at one level (shown as smaller dotted ellipse). From this, the system can initially search for voxels distal to most proximal hypoperfused level as a starting point to calculate the location, volume and shape of the hyperperfused volume. In FIG. 7H, this is shown as the volume defined between the two dotted ellipses (ie. a general frustoconcial shape). The detection of the location of MeVO is determined by analysis of proximal voxels that are contiguous with those L3 voxels as a likely location of an occlusion.

For illustrative purposes only, non-confluent voxels are shown which are unlikely to be present in a typical MeVO case.

MeVO Application

In various clinical settings, the MeVO tool can be used to assist in treatment/triaging decisions. As shown in FIG. 7G, a first level output 901 may simply provide output that MeVO likely exists. If this information is provided based on imaging conducted at a smaller center some distance from a main center, the diagnosing physician may be able to make an effective triaging decision to transfer the patient to the larger center, where the expertise in providing reperfusion treatment can be provided in a reasonable time frame. In this embodiment, the determination of MeVO may be based on various factors including the size, shape, location, confluence of the hypoperfused area and/or involvement of cortical grey matter and may include quantitative outputs regarding the likelihood of the diagnosis (e.g., 90% probability the occlusion is MeVO).

At other centers, particularly where treatment options may be available, additional outputs may be provided. These may include marking zones of interest as per analysis conducted at step 90h and/or conducting further analysis 90k that allows more specific identification of vessels of interest 90n.

Case Example

An 88-year-old female, arriving from home presented with expressive aphasia and mild right sided weakness since 2h; NIHSS on presentation: 10.

A perfusion map from CTP or a predictive perfusion map from mCTA as described above was obtained indicating an area of brain was hypoperfused.

The size and location characteristics of the hypoperfused area indicated a likely occluded vessel in an adjacent and proximal vessel. Based on the volume of tissue that is hypoperfused, an estimate of the size of vessel is made. The MeVO tool predicts and marks one or more areas where the occlusion is likely to be allowing the physician to quickly focus attention on those areas.

In various embodiments, past patient images are subjected to machine learning analysis to refine the precision of locating potential occlusion sites based on evaluations and variations across multiple past images.

As above, when the current patient images are introduced into the model, they are analyzed to find past patient images most correlated to the current images. As a result, the accuracy of predicting the location of the MeVO may be improved.

As shown in FIG. 7A for the above patient, an initial non-contrast CT scan was unremarkable. Following mCTA, a prediction map as shown in FIG. 7B was produced showing a specific hypoperfused region. Based on the relative position of the hypoperfused region, the MeVO tool determines and identifies a particular zone of interest in specific scan images as shown by hashed circles in FIG. 7C.

Additional analysis (manual or automatic) is conducted within that zone to identify an occluded vessel marked by the arrow in FIG. 7D. Depending on the protocols followed and for the purposes of illustration, occlusion was confirmed by conventional angiogram shown in FIG. 7E. Following reperfusion, follow-up imaging shows the opened vessel as shown in FIG. 7F.

Validation Study

As described above, Multiphase CT-Angiography (mCTA) provides time variant images of the pial vasculature supplying brain in patients with acute ischemic stroke (AIS). Described below is a machine learning (ML) technique that predicts infarct, penumbra and tissue perfusion from mCTA source images.

Study Methodology 284 patients with acute ischemic stroke (AIS) were included. All patients had non-contrast CT, mCTA and CTP imaging at baseline and follow up MRI/NCCT imaging. Of the 284 patient images, 140 patient images were randomly selected to train and validate three ML models to predict infarct, penumbra, and perfusion parameter on CTP, respectively. The remaining unseen 144 patient images independent of the derivation cohort were used to test the derived ML models. The predicted infarct, penumbra, and perfusion volume from ML models was spatially and volumetrically compared to manually contoured follow up infarct and time-dependent Tmax thresholded volume (CTP volume), using Bland-Altman plots, concordance correlation coefficient (CCC), intra-class correlation coefficient (ICC), and Dice similarity coefficient (DSC).

Study Results

Within the test cohort. Bland-Altman plots showed that the mean difference between the mCTA predicted infarct and follow up infarct was 21.7 mL (limit of agreement (LoA): −41.0 to 84.3 mL) in the 100 patients who had acute reperfusion (mTICI 2b/2c/3), and 3.4 mL (LoA: −66 to 72.9 mL) in the 44 patients who did not achieve reperfusion (mTICI 0/1). Amongst reperfused subjects. CCC was 0.4 [95% CI: 0.15-0.55, P<0.01] and ICC 0.42 [95% CI: 0.18-0.50, P<0.01]; in non-reperfused subjects CCC was 0.52 [95% CI: 0.2-0.6, P<0.001] and ICC 0.6 [95% CI: 0.37-0.76, P<0.001]. No difference was observed between the mCTA and CTP predicted infarct volume for the overall test cohort (P=0.67).

Multiphase CT Angiography is able to predict infarct, penumbra and tissue perfusion, comparable to CT perfusion imaging.

Study Background

Ischemic infarct core estimated using CT perfusion (CTP) at admission may be used in treatment decision making for patients with acute ischemic stroke (AIS).[1-4] Classification of infarct core and penumbra is achieved using tissue perfusion estimates derived using a deconvolution algorithm from repeated serial imaging. The mismatch ratio between salvageable tissue (penumbra) volume and infarct core volume can be used for selecting patients presenting beyond 6 hours and up to 24 hours from last known well.[3] CTP is limited by varying standardization of CTP parameter thresholds across different vendors, longer acquisition times and consequent susceptibility to patient motion, increased radiation dose, limited coverage (with some scanners) and the need for additional technical expertise to acquire the images.[5-7]

Multiphase computed tomographic angiography (mCTA) has been similarly used to select patients with AIS for endovascular therapy (EVT) in recent clinical trials. Advantages of this technique compared to CTP are simpler image acquisition, lower radiation exposure, no additional contrast compared to single-phase CTA, and whole-brain time-resolved images of pial arteries and veins beyond an occlusion while also determining thrombus location, size, vessel patency and tortuosity.[10, 11] Multiphase CTA imaging has not been as commonly used to predict ischemic tissue fate on a voxel by voxel basis, in the same way as CTP imaging. However, recent studies have demonstrated that mCTA can be used to predict tissue fate regionally, similar to CTP.[12-14] An ability to harness the advantages of mCTA while producing brain maps that estimate tissue perfusion and predict tissue fate is likely to be of significant clinical utility.

The study aimed to develop a machine learning based technique to estimate infarct core, penumbra and tissue perfusion in patients with acute ischemic stroke.

Study Materials and Methods

Data from the Prove-IT study (Precise and Rapid assessment of collaterals using multi-phase CTA in the triage of patients with acute ischemic stroke for IA Therapy), a multicenter study that acquired acute multimodal CT imaging including NCCT, multiphase CTA imaging (three phases), and CTP at baseline among ischemic stroke patients.[10, 12] This study was approved by the local institutional review board.

Study Participants

Figure 5A:
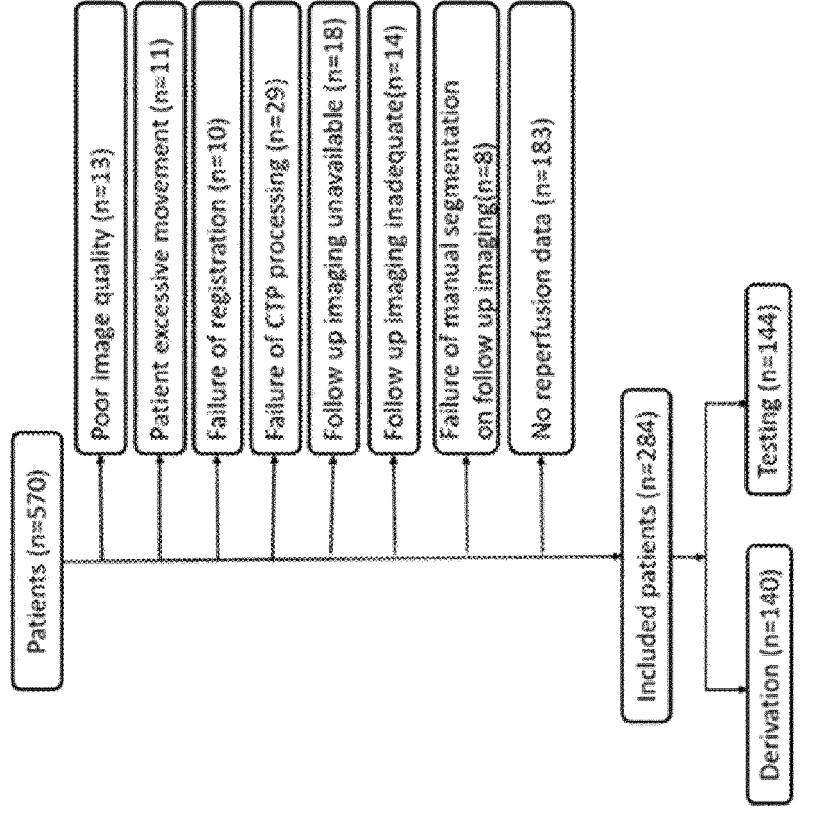
FIG. 5A is a flowchart showing details of patient inclusion.

Subjects who had (1) baseline non-contrast-enhanced CT (NCCT) and mCTA; (2) baseline CTP imaging with >=8 cm z-axis coverage; (3) had reperfusion assessed on conventional angiography after thrombolysis treatment (intravenous tPA, endovascular therapy, or both) with the modified thrombolysis in cerebral infarction [mTICI]); and (4) had 24/36-hour follow-up imaging on diffusion MRI or NCCT were included in this analysis. Patient inclusion and exclusion are shown in FIG. 5A. 284 patients, of whom, 196 patients had acute reperfusion (mTICI 2b/2c/3) and 88 patients did not (mTICI 0/1) were included.

Image Preprocessing

Each CTP study was processed using commercially available delay-insensitive deconvolution software (CT Perfusion 4D, GE Healthcare, Waukesha, WI). Absolute maps of cerebral blood flow (CBF, mL·min⁻¹·(100 g)⁻¹), cerebral blood volume (CBV, mL·(100 g)⁻¹), and Tmax (seconds) were generated. Average maps were created by averaging the dynamic CTP source images. Time-dependent Tmax thresholds confirmed previously, were used to generate baseline CTP thresholded maps (perfusion volume).[6, 7]

NCCT and mCTA images were first skull stripped.[15] Three-phase CTA images were then aligned using rigid-body registration to account for patient movement. The aligned 3-phase CTA images were registered onto NCCT images using affine registration. Two radiologists (>5 years' experience) used ITK-SNAP and consensus to manually delineate the infarct region on follow-up DWI/NCCT imaging.[16] The follow-up images along with manual infarct segmentations and CTP average maps were registered onto NCCT images, thus bringing all images into the same image space. When registration was sub-optimal, manual refinement of the registered infarct segmentations was attempted. The NiftyReg tool was used for all image registration tasks.[17]

Machine Learning Model

For the analysis, infarct core was defined as tissue that is infarcted on follow-up imaging even with reperfusion. Penumbra was defined as ischemic tissue that was not infarct core but infarcts on follow-up imaging when reperfusion is not achieved. These definitions of infarct core and penumbra are operational in context and not biological. The perfusion map used was a Tmax map thresholded using previously published time dependent thresholds.[6, 7]

Three machine learning models were developed: (1) Infarct model; (2) Penumbra model; and, (3) Perfusion model.

A 2-stage training mechanism was developed to train two machine learning models to predict infarctcore and penumbra respectively. The detailed training and testing strategy is shown in FIG. 3A.

Of 88 patients without acute reperfusion (mTICI 0/1), 44 patients (35 for training and 9 for validation) were randomly selected to derive a random forest classifier at the first stage for prediction of follow-up infarction in the non-reperfused patients (Penumbra model), while the remaining 44 patients with mTICI 0/1 independent of the derivation cohort were used to test this derived Penumbra Model. Of those 196 patients with mTICI 2b/2c/3, 96 patient images (70 for training and 26 for validation) randomly selected were first processed by the 1ˢᵗ stage Penumbra model, generating penumbra probability maps. These probability maps along with mCTA images were then used as inputs to derive the second random forest classifier at the second stage for infarct prediction (Infarct model) using follow up infarct manually segmented as a reference standard, while the remaining 100 patients with mTICI 2b/2c/3 reperfusion independent of the derivation cohort were used to test the derived Infarct Model. The final predictions are shown as infarct core and penumbra where penumbra is defined as affected tissue from the penumbra model minus affected tissue from the infarct core model (FIG. 5).

In order to show the ability of mCTA to estimate tissue perfusion at baseline compared to CTP imaging, the 140 patient images used for training and validating the Penumbra and Infarct models were reused to train and validate the third random forest classifier (Perfusion model). For deriving and testing this model, time dependent Tmax thresholded maps were used as reference standard.[6-7] The 144 images used for testing Penumbra and Infarct models independent on the derivation cohort were used to test the Perfusion model.

All three random forest models shared the same self-designed features as inputs. NCCT HU values were first subtracted from 3-phase CTA images, leading to a 3-point time intensity curve (TIC) for each voxel. Several features were extracted from the time intensity curve (TIC) for each voxel and used for deriving and testing the three random forest classifiers.

These include: 1) average and standard deviation of Hounsfield units (HUs) across 3-phase CTA images; 2) coefficient of variance of HUs in 3-phase CTA images; 3) changing slopes of HUs between any two phases; 4) peak of HUs in 3-phase CTA images; 5) time of peak HU.

All these features were calculated in the neighborhood centered at each voxel at three scales (3×3×3, 7×7×7, and 11×11×11 voxels) and then normalized using z-score method. The hyper-parameters for each random forest model, such as the number of trees in the forest and the maximum depth of trees, etc., were optimized using 5-fold cross validation using the respective validation cohort. Specifically, in 5-fold cross-validation, all the original samples are randomly partitioned into 5 equal sized subgroups. Of the 5 subgroups, a single subgroup is retained as the validation data for testing the model, and the remaining t subgroups are used as training data. The cross-validation process is then repeated 5 times, with each of the 5 subgroups used exactly once as the validation data. The 5 results can then be averaged to produce a single estimation. Class weight was set to account for the imbalanced sample distribution based on the ratio of positive and negative samples. The random forest classifiers derived from the training and validation dataset was then applied to the test cohort to generate a probability map for each patient. The probability map was then thresholded by a fixed value of 0.35, followed by image post-processing, such as isolated island removal and morphological operation, to generate the mCTA predicted volume. The thresholding value was optimized and determined from the validation cohort.

The fixed thresholding value of 0.35 was achieved by maximizing the Dice coefficients between the thresholded binary mask and reference standard of follow up infarct segmentation while varying different discrete thresholding values using the validation cohort. Isolated island removal was used to discard small clustered random noise in the thresholded binary mask. Morphological operation includes image erosion and dilation followed by hole-filling in the binary mask.

Statistical Methods

Expert contoured follow up lesion volume (Follow up infarct volume) were used as standard reference to evaluate mCTA predicted infarct core and penumbra volume for the test cohort. Time-dependent Tmax thresholded volumes (CTP volume) were used as standard reference to evaluate the mCTA perfusion volume for the test cohort. Bland-Altman plots were used to illustrate mean differences and limit of agreement (LoA) between mCTA predicted and follow up infarct volume, and CTP volume. Literal and relative volume agreement between mCTA predicted and follow up infarct volume, and CTP volume were also assessed using concordance correlation coefficient (CCC) and intra-class correlation coefficient (ICC), respectively. Spatial agreement between mCTA predicted volume and follow up infarct volume, and CTP volume was assessed using Dice similarity coefficient (DSC). Rank sum test was used to assess the difference between any non-normally distributed data. All statistical analyses were performed using MedCalc 17.8 (MedCalc Software, Mariakerke, Belgium) and Matiab (The MathWorks, Inc., United States). A two-sided alpha <0.05 was considered as statistically significant.

Study Results

Study Participants

Patient characteristics are summarized in Table 4. No differences were observed between the derivation and test cohorts (all P>0.05).

TABLE 4

Patient characteristics.

| Characteristics | Derivation cohort (N = 140) | Test cohort (N = 144) | P value |
|---|---|---|---|
| Median age, year (IQR) | 73 (62-79) | 72 (62-80) | .73 |
| Sex, n(%) male | 80 (57) | 77 (53) | .56 |
| Median baseline NIHSS (IQR) | 17 (7-23) | 14 (6-18) | .12 |
| Median baseline ASPECTS (IQR) | 9 (8-10) | 9 (8-10) | .15 |
| Median onset-to-imaging time, min (IQR) | 131 (94-226) | 139 (88-294) | .35 |
| Median imaging-to-reperfusion time, min (IQR) | 90 (68-115) | 87 (64-125) | .97 |
| Median onset-to-reperfusion time, min (IQR) | 245 (172-330) | 240 (181-377) | .71 |
| Median follow-up infarct volume, mL (IQR) | 22.2 (10.3-59.4) | 25.9 (10.1-60.6) | .60 |
| Site of occlusion, n(%) | | | |
| ICA | 22 (16) | 26 (18) | .76 |
| MCA: M1 | 73 (52) | 70 (48) | .64 |
| other | 45 (32) | 48 (33) | .63 |

IQR, interquartile range; NIHSS, National Institutes of Health Stroke Scale.
* p < 0.05.

Accuracy of mCTA In Predicting Follow up Infarct

Figure 8:
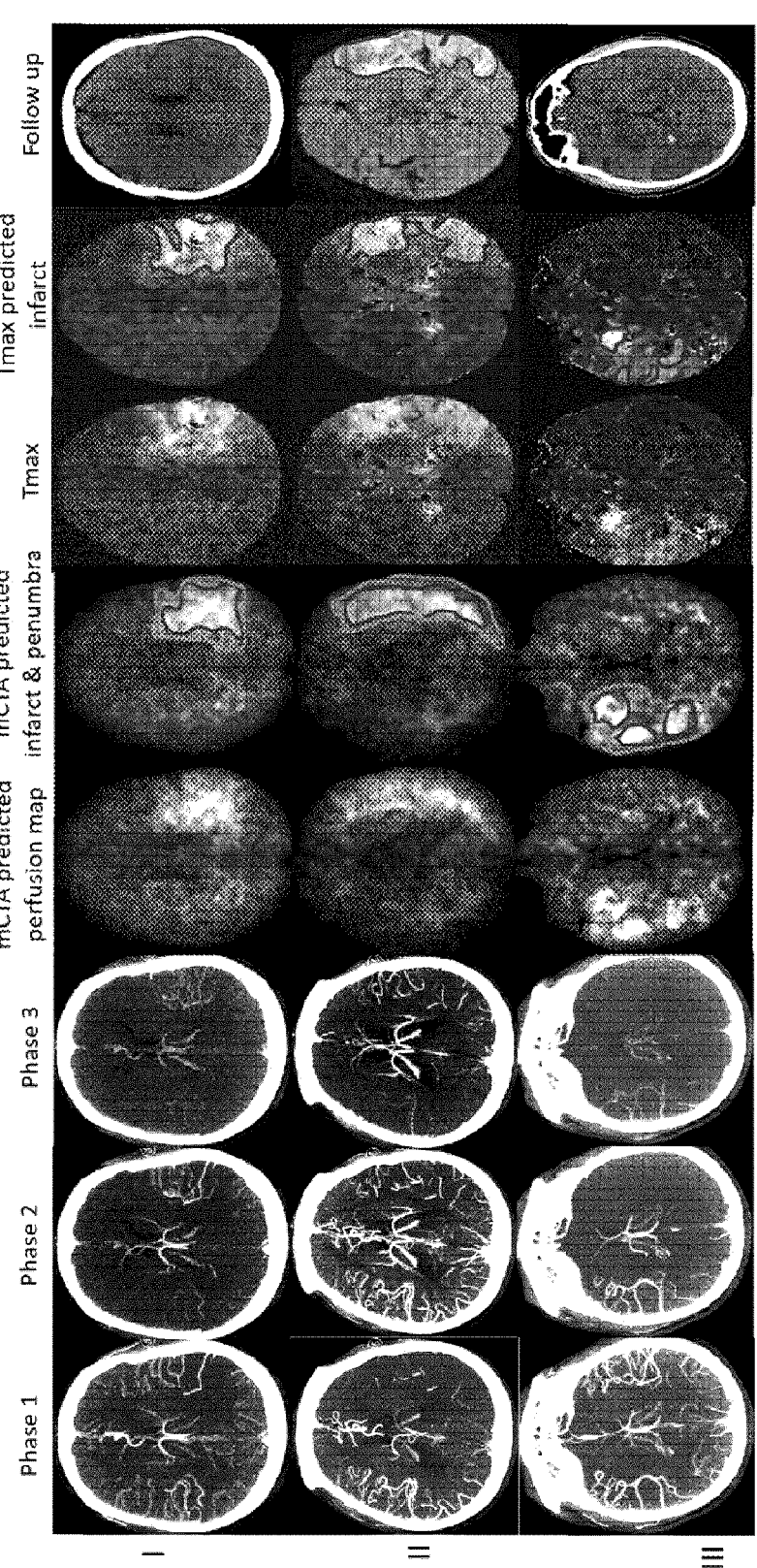
FIG. 8 shows multiphase CTA predicted infarct probability maps compared to CTP (Tmax) map and follow up infarct. There are 3 examples, each labelled as per rows.

FIG. 8 shows three examples of the mCTA prediction maps compared to CTP Tmax maps and follow up infarct. In particular, FIG. 8 shows multiphase CTA predicted infarct probability map compared to CTP (Tmax) map and follow-up infact. There are 3 examples, each labeled as per rows. Row I: patient with mTICI 2b, Row II: patient with mTICI 1, and Row III: patient with mTICI 3. Columns: mCTA phase 1 to 3, mCTA prediction perfusion maps, mCTA predicted infarct (red in column 5) and penumbra (blue in column 5) overlaid on the mCTA predicted perfusion map, CTP Tmax maps, time-dependent Tmax thresholds predicted infarct, infarct contoured in follow-up imaging, respectively. The penumbra is shown as affected tissue from the Penumbra model minus affected tissue from the Infarct model. Contour Color Code: inner or single contour "Red" R (core); outer contour—"Blue" B (penumbra). All areas within a red contour are red. All areas between a red contour and blue contour are blue.

Figure 8A:
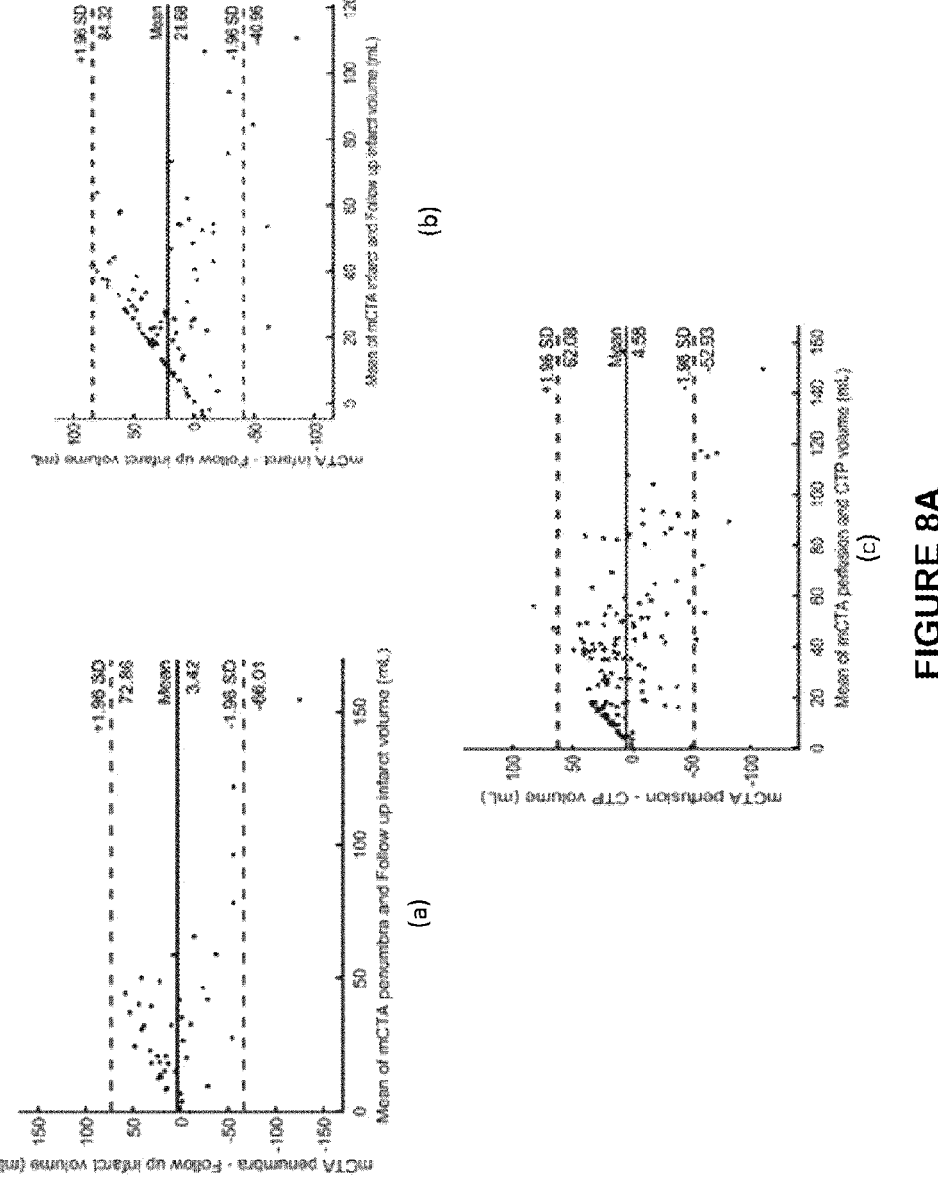
FIG. 8A show Bland-Altman plots of (a) mCTA penumbra volume predicted using the proposed model vs. follow up infarct volume for 44 patients who did not achieve acute reperfusion (mTICI 0/1); (b) mCTA infarct volume predicted using the proposed model vs. follow up infarct volume for 100 patients who had acute reperfusion (mTICI 2b/2c/3); and (c) mCTA perfusion volume predicted using the proposed model vs. time-dependent Tmax predicted infarct volume for all 144 patients in the test cohort.

FIG. 8A illustrates Bland-Altman plots (a) mCTA penumbra volume predicted using Penumbra model vs. follow-up infarct volume for 44 patients who did not achieve acute reperfusion (mTICI 0/1); (b) mCTA infarct volume predicted using Infarction model vs. follow-up infarct volume for 100 patients who had acute reperfusion (mTICI 2b/2c/3);

and (c) mCTA perfusion volume predicted using Perfusion model vs. time-dependent Tmax predicted infarct volume for all 144 patients in the test cohort. FIG. 8A(a) illustrates a Bland-Altman agreement plot between mCTA predicted infarct core+ penumbra volume and follow up infarct volume for the 44 patients who did not receive acute reperfusion (mTICI 0/1) in the test cohort. The mean difference between this mCTA predicted infarct core+penumbra volume (median, 33.2; IQR, 20.6-53.2 mL) and follow up infarct volume (median, 26.8; IQR, 12.3-54.8 mL) was 3.4 mL (LoA: −66-72.9 mL, P=0.69). The CCC between the two volumes was 0.52 [95% CI: 0.2-0.6. P<0.001] while the ICC was 0.6 [95% CI: 0.37-0.76, P<0.001]. The median DSC between the mCTA predicted lesion and follow up infarct was 26.5% (IQR, 12.9-39.3%).

FIG. 8A(b) illustrates a Bland-Altman agreement between the mCTA predicted infarct volume and follow up volume for 100 patients who achieved acute reperfusion (eTICI 2b/2c/3) in the test cohort. The mean difference between the mCTA infarct volume (median, 37; IQR, 23-58 mL) and follow up volume (median, 26; IQR, 13-54 mL) was 21.7 mL (LoA: −41.0-84.3 mL, P=0.48), CCC was 0.4 [95% CI: 0.15-0.55, P<0.01] and ICC 0.42 [95% CI: 0.18-0.50, P<0.01]. The median DSC between the mCTA infarct and follow up infarct was 24.7% (IQR, 13.8-30.4%).

The association between infarct volume predicted by the mCTA Infarct and Penumbra models and follow up infarct volume in the whole test cohort is shown in Table 5.

Accuracy of mCTA Predicting Perfusion Status

FIG. 8A(c) illustrates a Bland-Altman agreement between the mCTA predicted perfusion volume and CTP volume for 144 patients in the entire test cohort. The mean difference between the mCTA perfusion (median, 40.5; IQR, 22.9-59 mL) and CTP volume (median, 26.9; IQR, 6.7-56.7 mL) was 4.6 mL (LoA: −53-62.1 mL, P=0.56), CCC was 0.63 [95% CI: 0.53-0.71, P<0.01] and ICC was 0.68 [95% CI: 0.58-0.78, P<0.001]. The median DSC between mCTA predicted perfusion and CTP volume was 40.5% (IQR, 25.7-52.7%).

The association between the volume predicted by mCTA perfusion model and follow up infarct volume, and between the time dependent Tmax thresholded predicted infarct volume and follow up infarct volume in the whole test cohort is shown in Table 5.

TABLE 5

Comparisons between infarct volumes predicted by the derived mCTA models and CTP vs. follow up infarct volume (median, 24.8; IQR, 10.5-58.8 mL) in the test cohort (n = 144).

| | mCTA Infarct and Penumbra model | mCTA Perfusion model | Time dependent Tmax thresholded model (CTP) | P value |
|---|---|---|---|---|
| Predicted volume (median [IQR], mL) | 37.3 [21.3, 57.8] | 40.5 [22.9, 63] | 38.3 [15.0, 65.5] | .67 |
| Volume difference# (mean [LoA], mL) | 21.7 [−44, 86.3] | 20.4 [−51.3, 92.1] | 22.3 [−42.6, 87.2] | .45 |
| DSC (median [IQR], %) | 22.5 [13.8, 30.4] | 21.7 [10.9, 31.2] | 23.2 [13.9, 33] | .55 |
| CCC [95% CI] | 0.43 [0.18-0.58] | 0.41 [0.16-0.62] | 0.45 [0.32-0.54] | N/A |

TABLE 5-continued

Comparisons between infarct volumes predicted by the derived mCTA models and CTP vs. follow up infarct volume (median, 24.8; IQR, 10.5-58.8 mL) in the test cohort (n = 144).

| | mCTA Infarct and Penumbra model | mCTA Perfusion model | Time dependent Tmax thresholded model (CTP) | P value |
|---|---|---|---|---|
| ICC [CI] | 0.5 [0.29-0.64] | 0.47 [0.3-0.56] | 0.54 [0.3-0.64] | N/A |

IQR, interquartile range; LoA, limit of agreement; CI, confidence interval; DSC: Dice similarity coefficient between the predicted volume and follow up infarct volume; CCC: concordance correlation coefficient; ICC: intra-class correlation coefficient.
N/A: Not applicable.
Volume difference is defined as follow up infarct volume minus model prediction, generated from Bland-Altman analysis Study Discussion Multiphase CT angiography (mCTA) is a quick and easy-to-use imaging tool in selecting patients with acute ischemic stroke (AIS) for revascularization therapy.[10] The developed machine learning technique described in this study shows that tissue status can be automatically predicted from the mCTA just as it is currently done using CT perfusion imaging. These results demonstrate that mCTA using the methods proposed here has similar ability to CTP imaging in predicting tissue fate.

As such, the methodologies described herein can help physicians make clinical decisions regarding acute stroke treatment, especially in hospitals without CTP capabilities.

When comparing mCTA predicted infarct volume with follow up infarct volume in patients who achieved acute reperfusion (mTICI 2b/2c/3), the mean volume difference of 21.7 mL, CCC of 0.4, and ICC of 0.42 are fair. The mCTA predicted infarct volume agrees better with follow up infarct volume in patients who did not achieve acute reperfusion (mTICI 0/1/2) with a mean volume difference of 3.4 mL, CCC of 0.52, and ICC of 0.6. DSCs between mCTA predicted infarct and penumbra and follow up volume are relatively low (less than 30%). However, accurate spatial quantification of infarction in patients with AIS is complicated and likely influenced by many pathophysiological factors, such as collateral status, tissue tolerance to ischemia/hypoxia, cerebral autoregulation, leukoaraiosis, fluctuation in blood pressure, hyperglycemia and time to reperfusion.[6, 7, 8] All these factors likely lead to discrepancy between infarct volume predicted at baseline and follow up imaging.

Of note, a recent paper from the HERMES group that used validated CTP software (i.e. RAPID, iSchemaView, Menlo Park, CA) showed similar DSC (median, 0.24; IQR, 0.15-0.37) between CTP predicted infarct volume and follow up infarct volume.[19] When comparing mCTA predicted perfusion maps with CTP time dependent Tmax thresholded maps, the results show stronger agreement between the two measurements with a mean volume difference of 4.6 mL, CCC of 0.63, and ICC of 0.68. The median DSC of 40.5% between the mCTA predicted perfusion and CTP volume was also reasonable, suggesting good spatial overlap.

Imaging paradigms currently used in selecting patients with AIS for treatment include non-contrast CT, single-phase CTA, or CTP. CTP, however, requires additional radiation and contrast and specific acquisition protocols that are different from NCCT and CTA. CTP is sensitive to patient motion, a feature that invalidates that tool in almost 10 to 25% of patients.[20] Eleven patients were excluded from this study as CTP maps generated by the software were corrupted due to the excessive patient motion during acquisition (FIG. 5A). Multiphase CTA is potentially less prone to patient motion while being capable of predicting perfusion maps appropriately (Supplements: FIG. 5A). CTP also adds additional costs to the health system that include cost of the scan and resources allocated to training personnel to acquire the scan.[21, 22] Multiphase CTA has minimal additional radiation, no additional contrast material, whole-brain coverage, relative insensitivity to patient motion and minimal additional cost to acquire over a single phase CTA.[10, 12, 13] The technique described here automates mCTA interpretation and provides physicians with tissue prediction as well as perfusion maps, just as CTP imaging does, thus potentially increasing their confidence in decision making (Table 5). FIG. 8 shows an example of penumbra and infarct core (and mismatch) predicted using mCTA. Of note, physiological definitions of infarct and penumbra are different from the operational definitions used in this study. Unlike conventional mCTA but similar to CTP, the technique described in the study is capable of detecting smaller perfusion lesions in the entire brain including the posterior circulation (Supplements: FIG. 8).

A strength of the developed machine learning technique is that it does not rely on deconvolution algorithms, which plays an essential role in current CTP processing. Although deconvolution methods can appropriately model perfusion status, the introduction of physiological variations in arterial delivery of contrast, the effects of collateral flow, and venous outflow components of cerebral perfusion, greatly increase the computational complexity.[23, 24] The number of variables and the algorithms used to calculate these variables results in variability in generating CTP threshold values for estimating infarct and penumbra across different vendor software. Additionally, numerical solutions to deconvolution greatly relies on accurate selection of artery input function (AIF), a parameter that is case dependent and sensitive to noise, especially given the low signal to noise ratio of perfusion images, even when preprocessing, such as motion correction, temporal and spatial smoothing, and deconvolution regularization are applied.[25, 26] The deconvolution free approach developed in this study can be easily integrated into any imaging paradigm using NCCT and mCTA as a post-processing step, potentially obviating the need for CTP.

In conclusion, infarct core, penumbra, and perfusion status can be automatically predicted from multiphase CTA imaging using machine learning. This technique shows comparable accuracy to CT perfusion imaging in measuring tissue status in patients with acute ischemic stroke. This work has the potential of assisting physicians in making treatment decisions in clinical settings.

Although the present invention has been described and illustrated with respect to preferred embodiments and preferred uses thereof, it is not to be so limited since modifications and changes can be made therein which are within the full, intended scope of the invention as understood by those skilled in the art.

The invention claimed is:

1. A method of deriving and presenting information useful in diagnosing medium vessel occlusion (MeVO) in a current patient comprising the steps of:
   from a plurality of CT images showing hypoperfused regions of the current patient;
   i. quantifying, by one or more processors, a hypoperfused tissue volume in the current patient;
   ii. comparing, by the one or more processors the hypoperfused tissue volume from step i to threshold volume parameters defining a MeVO event and determining if the hypoperfused tissue matches volume parameters of a MeVO event; and, iii. if a MeVO event is determined, electronically displaying on a display device a MeVO event determination.

2. The method as in claim 1 wherein steps i and ii include quantifying, by the one or more processors, a hypoperfused tissue shape in the current patient and comparing, by the one or more processors, the hypoperfused tissue shape to threshold shape parameters defining a MeVO event and determining, by the one or more processors, if the hypoperfused tissue shape matches shape parameters of a MeVO event.

3. The method as in any one of claim 1 wherein steps i and ii include quantifying, by the one or more processors, a hypoperfused tissue location in the current patient and comparing, by the one or more processors the hypoperfused tissue location to threshold location parameters defining a MeVO event and determining, by the one or more processors, if the hypoperfused tissue location matches location parameters of a MeVO event.

4. The method as in any one of claim 3 further comprising the steps of correlating, by the one or more processors, the hypoperfused tissue location to corresponding hypoperfused locations from historical patient data wherein historical patient data includes data marking past MeVO events; determining, by the one or more processors, a best fit of historical patient image data and electronically marking and displaying current patient images with MeVO location data derived from the historical patient image data.

5. The method as in claim 4 wherein the historical patient data with past MeVO events includes data quantifying proximal voxel location relevant to a past MeVO event within a past patient record.

6. The method as in claim 4 wherein historical patient data records have been previously analyzed to derive 2D and/or 3D relationships between level 1-3 vessels.

7. The method as in claim 6 wherein the historical patient data records have been previously analyzed to define volumes of tissue as level 1, level 2 or level 3 tissue and wherein each volume of level 1, level 2 or level 3 tissue has at least one, equal, distal or proximal relationship with an adjacent volume of tissue.

8. The method as in claim 7 further comprising the step of, after step iii, examining, by the one or more processors, changes in contrast densities in adjacent proximal volumes across two or more phases of CTA images for the current patient and based on those changes electronically marking and displaying changes in contrast density as normal flow or abnormal flow.

9. The method as in claim 8 further comprising the step of discarding, by the one or more processors, volumes showing normal flow from further analysis.

10. The method as in claim 9 further comprising the step of utilizing, by the one or more processors, volumes showing normal flow as a baseline for contrast density analysis.

11. The method as in claim 10 further comprising the step of electronically marking and displaying, by the one or more processors, volumes showing abnormal flow for further analysis.

12. The method as in claim 11 further comprising the step of analyzing, by the one or more processors, zones where contrast abruptly transitions from no contrast to significant contrast between adjacent images or vice versa to identify vessels of interest.

13. The method as in claim 12 further comprising the step of electronically marking and displaying, by the one or more processors, zones where contrast abruptly transitions on CTA images of the current patient.

14. The method as in any one of claim 1 wherein steps i and ii include quantifying, by the one or more processors, involved cortex.

15. The method as in any one of claim 1 wherein steps i and ii include quantifying, by the one or more processors, hypoperfused tissue confluence in the current patient and comparing, by the one or more processors, the hypoperfused tissue confluence to hypoperfused tissue confluence parameters defining a MeVO event and determining, by the one or more processors, if the hypoperfused tissue confluence matches hypoperfused tissue confluence of a MeVO event.

16. The method as in claim 1 further comprising the steps of providing, by the one or more processors, at least one output selected from any one of or a combination of: a) presence or not of MeVO; b) zone of interest marking and c) vessel of interest.

17. A method of deriving and presenting information useful in diagnosing medium vessel occlusion (MeVO) in a current patient comprising the steps of:

from a plurality of CTA images showing at least one hypoperfused region of the current patient;

i. identifying, by one or more processors, the at least one hypoperfused region and correlating, by the one or more processors, the at least one hypoperfused regions to one or more corresponding hypoperfused regions from within historical patient data; and, ii. deriving and identifying, by the one or more processors, immediately proximal vessels/zones in the current patient based on best match(s) to the historical patient data and electronically marking and displaying the proximal vessel/ zones as predicted MeVO locations on current patient CT images.

18. The method as in claim 17 where the CT images are mCTA images.

19. The method as in claim 17 further comprising the steps of quantifying, by the one or more processors, a hypoperfused tissue shape in the current patient and comparing, by the one or more processors, the hypoperfused tissue shape to threshold shape parameters defining a MeVO event and determining, by the one or more processors, if the hypoperfused tissue shape matches shape parameters of a MeVO event.

20. The method as in any one of claim 17 further comprising the steps of quantifying, by the one or more processors, a hypoperfused tissue location in the current patient and comparing, by the one or more processors, the hypoperfused tissue location to threshold location parameters defining a MeVO event and determining, by the one or more processors, if the hypoperfused tissue location matches location parameters of a MeVO event.

21. The method as in any one of claim 17 further comprising the steps of quantifying, by the one or more processors, involved cortex.

22. The method as in any one of claim 17 further comprising the steps of quantifying, by the one or more processors, hypoperfused tissue confluence in the current patient and comparing, by the one or more processors, the hypoperfused tissue confluence to hypoperfused tissue confluence parameters defining a MeVO event and determining, by the one or more processors, if the hypoperfused tissue confluence matches hypoperfused tissue confluence of a MeVO event.

23. The method as in any one of claim 17 further comprising the steps of correlating, by the one or more processors, the hypoperfused tissue location to corresponding hypoperfused locations from historical patient data wherein historical patient data includes data marking past MeVO events; determining, by the one or more processors, a best fit of historical patient image data and electronically marking and displaying current patient images with MeVO location data derived from the historical patient image data.

24. The method as in claim 23 wherein the historical patient data with past MeVO events includes data quantifying proximal voxel location relevant to a past MeVO event within a past patient record.

\* \* \* \* \*